US011510632B2

(12) United States Patent
Begin et al.

(10) Patent No.: US 11,510,632 B2
(45) Date of Patent: Nov. 29, 2022

(54) SYSTEMS FOR INDICATING PARAMETERS IN AN IMAGING DATA SET AND METHODS OF USE

(71) Applicant: PHILIPS IMAGE GUIDED THERAPY CORPORATION, San Diego, CA (US)

(72) Inventors: Elizabeth Begin, Bellerica, MA (US); Joseph Burnett, Carlsbad, CA (US); Nathaniel J. Kemp, Concord, MA (US); Anuja Nair, San Diego, CA (US); Timothy K. Glynn, San Diego, CA (US); Jason Sproul, Watertown, MA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 88 days.

(21) Appl. No.: 16/798,412

(22) Filed: Feb. 23, 2020

(65) Prior Publication Data
US 2020/0205750 A1 Jul. 2, 2020

Related U.S. Application Data

(63) Continuation of application No. 14/044,987, filed on Oct. 3, 2013, now Pat. No. 10,568,586.
(Continued)

(51) Int. Cl.
*A61B 5/00* (2006.01)
*A61B 8/12* (2006.01)
(Continued)

(52) U.S. Cl.
CPC .......... *A61B 5/7435* (2013.01); *A61B 5/0035* (2013.01); *A61B 5/0066* (2013.01);
(Continued)

(58) Field of Classification Search
CPC ....... A61B 5/7435; A61B 8/466; A61B 5/489; A61B 5/743; A61B 5/0066; A61B 8/483;
(Continued)

(56) References Cited

U.S. PATENT DOCUMENTS 3,301,258 A 1/1967 Werner
3,617,880 A 11/1971 Cormack et al.
(Continued)

FOREIGN PATENT DOCUMENTS

EP 1041373 A2 10/2000
EP 01172637 A1 1/2002
(Continued)

OTHER PUBLICATIONS

Siemens, "Navigotor Snygo Operator Manual SOMATOM Emotion Duo Version A40A", Jan. 2000.
(Continued)

*Primary Examiner* — Bo Joseph Peng

(57) ABSTRACT

Systems and methods for aiding users in viewing, assessing and analyzing images, especially images of lumens and medical devices contained within the lumens. Systems and methods for interacting with images of lumens and medical devices, for example through a graphical user interface.

19 Claims, 24 Drawing Sheets

Related U.S. Application Data

(60) Provisional application No. 61/710,419, filed on Oct. 5, 2012.

(51) Int. Cl.

| | | |
|---|---|---|
| *A61B 8/08* | (2006.01) | |
| *A61B 6/00* | (2006.01) | |
| *G01R 33/28* | (2006.01) | |
| *A61B 6/12* | (2006.01) | |
| *A61B 5/02* | (2006.01) | |
| *A61B 5/021* | (2006.01) | |
| *A61F 2/82* | (2013.01) | |
| *A61B 5/06* | (2006.01) | |
| *A61B 8/00* | (2006.01) | |
| *G06T 11/00* | (2006.01) | |
| *G06T 19/20* | (2011.01) | |
| *G01R 33/48* | (2006.01) | |
| *A61B 5/026* | (2006.01) | |
| *A61B 8/14* | (2006.01) | |
| *G01R 33/56* | (2006.01) | |

(52) U.S. Cl.
CPC ............ *A61B 5/0095* (2013.01); *A61B 5/021* (2013.01); *A61B 5/02007* (2013.01); *A61B 5/066* (2013.01); *A61B 5/489* (2013.01); *A61B 5/743* (2013.01); *A61B 5/746* (2013.01); *A61B 5/7455* (2013.01); *A61B 5/7475* (2013.01); *A61B 6/12* (2013.01); *A61B 6/504* (2013.01); *A61B 8/0841* (2013.01); *A61B 8/12* (2013.01); *A61B 8/4416* (2013.01); *A61B 8/465* (2013.01); *A61B 8/466* (2013.01); *A61B 8/483* (2013.01); *A61B 8/5223* (2013.01); *A61F 2/82* (2013.01); *G01R 33/285* (2013.01); *G06T 11/001* (2013.01); *G06T 19/20* (2013.01); *A61B 5/0261* (2013.01); *A61B 5/0263* (2013.01); *A61B 8/14* (2013.01); *A61B 8/5261* (2013.01); *G01R 33/4814* (2013.01); *G01R 33/5608* (2013.01); *G06T 2210/41* (2013.01); *G06T 2219/2012* (2013.01)

(58) Field of Classification Search
CPC ....... A61B 8/12; A61B 8/0841; A61B 5/0035; A61B 6/504; A61B 5/0095; A61B 6/12; A61B 8/5223; A61B 5/02007; A61B 5/021; A61B 5/7475; A61B 5/746; A61B 5/7455; A61B 5/066; A61B 8/4416; A61B 8/465; A61B 8/5261; A61B 8/14; A61B 5/0263; A61B 5/0261; G06T 11/001; G06T 19/20; G06T 2210/41; G06T 2219/2012; G01R 33/285; G01R 33/5608; G01R 33/4814; A61F 2/82; G16H 50/30
See application file for complete search history.

(56) References Cited

U.S. PATENT DOCUMENTS

| | | |
|---|---|---|
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |
| 4,344,438 A | 8/1982 | Schultz |
| 4,398,791 A | 8/1983 | Dorsey |
| 4,432,370 A | 2/1984 | Hughes et al. |
| 4,552,554 A | 11/1985 | Gould et al. |
| 4,577,543 A | 3/1986 | Wilson |
| 4,676,980 A | 6/1987 | Segal et al. |
| 4,682,895 A | 7/1987 | Costello |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |

(56) References Cited

U.S. PATENT DOCUMENTS

| | | |
|---|---|---|
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelll |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,925,055 A | 7/1999 | Adrian et al. |
| 5,949,929 A | 9/1999 | Hamm |
| 5,951,586 A | 9/1999 | Berg et al. |
| 5,974,521 A | 10/1999 | Akerlb |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |

(56) References Cited

U.S. PATENT DOCUMENTS

| | | |
|---|---|---|
| 6,387,124 B1 | 5/2002 | Buscemi et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,685,648 B2 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |
| 6,709,444 B1 | 3/2004 | Makower |
| 6,712,836 B1 | 3/2004 | Berg et al. |
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B1 | 4/2006 | Ruffa |
| 7,027,743 B1 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,291,146 B2 | 11/2007 | Steinke et al. |

(56) References Cited

U.S. PATENT DOCUMENTS

| | | | |
|---|---|---|---|
| 7,292,715 | B2 | 11/2007 | Furnish |
| 7,292,885 | B2 | 11/2007 | Scott et al. |
| 7,294,124 | B2 | 11/2007 | Eidenschink |
| 7,300,460 | B2 | 11/2007 | Levine et al. |
| 7,335,161 | B2 | 2/2008 | Von Arx et al. |
| 7,337,079 | B2 | 2/2008 | Park et al. |
| 7,355,716 | B2 | 4/2008 | de Boer et al. |
| 7,356,367 | B2 | 4/2008 | Liang et al. |
| 7,358,921 | B2 | 4/2008 | Snyder et al. |
| 7,359,062 | B2 | 4/2008 | Chen et al. |
| 7,359,554 | B2 | 4/2008 | Klingensmith et al. |
| 7,363,927 | B2 | 4/2008 | Ravikumar |
| 7,366,376 | B2 | 4/2008 | Shishkov et al. |
| 7,382,949 | B2 | 6/2008 | Bouma et al. |
| 7,387,636 | B2 | 6/2008 | Cohn et al. |
| 7,391,520 | B2 | 6/2008 | Zhou et al. |
| 7,397,935 | B2 | 7/2008 | Kimmel et al. |
| 7,399,095 | B2 | 7/2008 | Rondinelli |
| 7,408,648 | B2 | 8/2008 | Kleen et al. |
| 7,414,779 | B2 | 8/2008 | Huber et al. |
| 7,440,087 | B2 | 10/2008 | Froggatt et al. |
| 7,447,388 | B2 | 11/2008 | Bates et al. |
| 7,449,821 | B2 | 11/2008 | Dausch |
| 7,450,165 | B2 | 11/2008 | Ahiska |
| RE40,608 | E | 12/2008 | Glover et al. |
| 7,458,967 | B2 | 12/2008 | Appling et al. |
| 7,463,362 | B2 | 12/2008 | Lasker et al. |
| 7,463,759 | B2 | 12/2008 | Klingensmith et al. |
| 7,491,226 | B2 | 2/2009 | Palmaz et al. |
| 7,515,276 | B2 | 4/2009 | Froggatt et al. |
| 7,527,594 | B2 | 5/2009 | Vardl et al. |
| 7,534,251 | B2 | 5/2009 | WasDyke |
| 7,535,797 | B2 | 5/2009 | Peng et al. |
| 7,547,304 | B2 | 6/2009 | Johnson |
| 7,564,949 | B2 | 7/2009 | Sattler et al. |
| 7,577,471 | B2 | 8/2009 | Camus et al. |
| 7,583,857 | B2 | 9/2009 | Xu et al. |
| 7,603,165 | B2 | 10/2009 | Townsend et al. |
| 7,612,773 | B2 | 11/2009 | Magnin et al. |
| 7,633,627 | B2 | 12/2009 | Choma et al. |
| 7,645,229 | B2 | 1/2010 | Armstrong |
| 7,658,715 | B2 | 2/2010 | Park et al. |
| 7,660,452 | B2 | 2/2010 | Zwirn et al. |
| 7,660,492 | B2 | 2/2010 | Bates et al. |
| 7,666,204 | B2 | 2/2010 | Thornton et al. |
| 7,672,790 | B2 | 3/2010 | McGraw et al. |
| 7,680,247 | B2 | 3/2010 | Atzinger et al. |
| 7,684,991 | B2 | 3/2010 | Stohr et al. |
| 7,711,413 | B2 | 5/2010 | Feldman et al. |
| 7,720,322 | B2 | 5/2010 | Prisco |
| 7,728,986 | B2 | 6/2010 | Lasker et al. |
| 7,734,009 | B2 | 6/2010 | Brunner et al. |
| 7,736,317 | B2 | 6/2010 | Stephens et al. |
| 7,742,795 | B2 | 6/2010 | Stone et al. |
| 7,743,189 | B2 | 6/2010 | Brown et al. |
| 7,762,954 | B2 | 7/2010 | Nix et al. |
| 7,766,896 | B2 | 8/2010 | Kornkven Volk et al. |
| 7,773,792 | B2 | 8/2010 | Kimmel et al. |
| 7,775,981 | B1 | 8/2010 | Guracar et al. |
| 7,777,399 | B2 | 8/2010 | Eidenschink et al. |
| 7,781,724 | B2 | 8/2010 | Childers et al. |
| 7,783,337 | B2 | 8/2010 | Feldman et al. |
| 7,787,127 | B2 | 8/2010 | Galle et al. |
| 7,792,342 | B2 | 9/2010 | Barbu et al. |
| 7,801,343 | B2 | 9/2010 | Unal et al. |
| 7,801,590 | B2 | 9/2010 | Feldman et al. |
| 7,813,609 | B2 | 10/2010 | Petersen et al. |
| 7,831,081 | B2 | 11/2010 | Li |
| 7,846,101 | B2 | 12/2010 | Eberle et al. |
| 7,853,104 | B2 | 12/2010 | Oota et al. |
| 7,853,316 | B2 | 12/2010 | Milner et al. |
| 7,860,555 | B2 | 12/2010 | Saadat |
| 7,862,508 | B2 | 1/2011 | Davies et al. |
| 7,872,759 | B2 | 1/2011 | Tearney et al. |
| 7,880,868 | B2 | 2/2011 | Aoki |
| 7,881,763 | B2 | 2/2011 | Brauker et al. |
| 7,909,844 | B2 | 3/2011 | Alkhatib et al. |
| 7,921,854 | B2 | 4/2011 | Hennings et al. |
| 7,927,784 | B2 | 4/2011 | Simpson |
| 7,929,148 | B2 | 4/2011 | Kemp |
| 7,930,014 | B2 | 4/2011 | Huennekens et al. |
| 7,930,104 | B2 | 4/2011 | Baker et al. |
| 7,936,462 | B2 | 5/2011 | Jiang et al. |
| 7,942,852 | B2 | 5/2011 | Mas et al. |
| 7,947,012 | B2 | 5/2011 | Spurchise et al. |
| 7,951,186 | B2 | 5/2011 | Eidenschink et al. |
| 7,952,719 | B2 | 5/2011 | Brennan, III |
| 7,972,353 | B2 | 7/2011 | Hendriksen et al. |
| 7,976,492 | B2 | 7/2011 | Brauker et al. |
| 7,977,950 | B2 | 7/2011 | Maslen |
| 7,978,916 | B2 | 7/2011 | Klingensmith et al. |
| 7,981,041 | B2 | 7/2011 | McGahan |
| 7,981,151 | B2 | 7/2011 | Rowe |
| 7,983,737 | B2 | 7/2011 | Feldman et al. |
| 7,993,333 | B2 | 8/2011 | Oral et al. |
| 7,995,210 | B2 | 8/2011 | Tearney et al. |
| 7,996,060 | B2 | 8/2011 | Trofimov et al. |
| 7,999,938 | B2 | 8/2011 | Wang |
| 8,021,377 | B2 | 9/2011 | Eskuri |
| 8,021,420 | B2 | 9/2011 | Dolan |
| 8,036,732 | B2 | 10/2011 | Milner |
| 8,040,586 | B2 | 10/2011 | Smith et al. |
| 8,047,996 | B2 | 11/2011 | Goodnow et al. |
| 8,049,900 | B2 | 11/2011 | Kemp et al. |
| 8,050,478 | B2 | 11/2011 | Li et al. |
| 8,050,523 | B2 | 11/2011 | Younge et al. |
| 8,052,605 | B2 | 11/2011 | Muller et al. |
| 8,057,394 | B2 | 11/2011 | Dala-Krishna |
| 8,059,923 | B2 | 11/2011 | Bates et al. |
| 8,070,800 | B2 | 12/2011 | Lock et al. |
| 8,080,800 | B2 | 12/2011 | Hoctor et al. |
| 8,088,102 | B2 | 1/2012 | Adams et al. |
| 8,100,838 | B2 | 1/2012 | Wright et al. |
| 8,104,479 | B2 | 1/2012 | Glynn et al. |
| 8,108,030 | B2 | 1/2012 | Castella et al. |
| 8,114,102 | B2 | 2/2012 | Galdonik et al. |
| 8,116,605 | B2 | 2/2012 | Petersen et al. |
| 8,125,648 | B2 | 2/2012 | Milner et al. |
| 8,126,239 | B2 | 2/2012 | Sun et al. |
| 8,133,199 | B2 | 3/2012 | Weber et al. |
| 8,133,269 | B2 | 3/2012 | Flechsenhar et al. |
| 8,140,708 | B2 | 3/2012 | Zaharia et al. |
| 8,148,877 | B2 | 4/2012 | Jiang et al. |
| 8,167,932 | B2 | 5/2012 | Bourang et al. |
| 8,172,757 | B2 | 5/2012 | Jaffe et al. |
| 8,177,809 | B2 | 5/2012 | Mavani et al. |
| 8,187,191 | B2 | 5/2012 | Hancock et al. |
| 8,187,267 | B2 | 5/2012 | Pappone et al. |
| 8,187,830 | B2 | 5/2012 | Hu et al. |
| 8,199,218 | B2 | 6/2012 | Lee et al. |
| 8,206,429 | B2 | 6/2012 | Gregorich et al. |
| 8,208,995 | B2 | 6/2012 | Tearney et al. |
| 8,222,906 | B2 | 7/2012 | Wyar et al. |
| 8,233,681 | B2 | 7/2012 | Aylward et al. |
| 8,233,718 | B2 | 7/2012 | Klingensmith et al. |
| 8,238,624 | B2 | 8/2012 | Doi et al. |
| 8,239,938 | B2 | 8/2012 | Simeral et al. |
| 8,277,386 | B2 | 10/2012 | Ahmed et al. |
| 8,280,470 | B2 | 10/2012 | Milner et al. |
| 8,289,284 | B2 | 10/2012 | Glynn et al. |
| 8,289,522 | B2 | 10/2012 | Tearney et al. |
| 8,298,147 | B2 | 10/2012 | Huennekens et al. |
| 8,298,149 | B2 | 10/2012 | Hastings et al. |
| 8,301,000 | B2 | 10/2012 | Sillard et al. |
| 8,309,428 | B2 | 11/2012 | Lemmerhirt et al. |
| 8,317,713 | B2 | 11/2012 | Davies et al. |
| 8,323,201 | B2 | 12/2012 | Towfiq et al. |
| 8,329,053 | B2 | 12/2012 | Martin et al. |
| 8,336,643 | B2 | 12/2012 | Harleman |
| 8,349,000 | B2 | 1/2013 | Schreck |
| 8,353,945 | B2 | 1/2013 | Andreas et al. |
| 8,353,954 | B2 | 1/2013 | Cai et al. |
| 8,357,981 | B2 | 1/2013 | Martin et al. |
| 8,361,097 | B2 | 1/2013 | Patel et al. |

(56) References Cited

U.S. PATENT DOCUMENTS

| | | |
|---|---|---|
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0048345 A1 | 12/2001 | Stanley et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0249270 A1 | 12/2004 | Kondo |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0065432 A1 | 3/2005 | Kimura |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childlers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |

(56) References Cited

U.S. PATENT DOCUMENTS

| | | |
|---|---|---|
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036404 A1* | 2/2007 | Li .......................... A61B 8/12 382/128 |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0258632 A1 | 11/2007 | Friedman |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0055308 A1 | 3/2008 | Decker |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Olman et al. |
| 2009/0306520 A1 | 12/2009 | Schmitt |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0081931 A1 | 4/2010 | Cloutier |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |

(56) References Cited

U.S. PATENT DOCUMENTS

| | | |
|---|---|---|
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0071404 A1* | 3/2011 | Schmitt .............. A61B 5/02007 382/128 |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0263960 A1 | 10/2011 | Mitchell |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg et al. |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2438877 A2 | 4/2012 |
| GB | 2280261 A | 1/1995 |
| JP | 2000-262461 A | 9/2000 |
| JP | 2000-292260 A | 10/2000 |

(56) References Cited

FOREIGN PATENT DOCUMENTS

| | | |
|---|---|---|
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2005-274380 A | 10/2005 |
| JP | 2006167287 A | 6/2006 |
| JP | 2006-184284 A | 7/2006 |
| JP | 2006-266797 A | 10/2006 |
| JP | 2006-313158 A | 11/2006 |
| JP | 2007-024677 A | 1/2007 |
| JP | 2009-233001 A | 10/2009 |
| JP | 2009-536425 A | 10/2009 |
| JP | 2011-56786 A | 3/2011 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/044296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 11/2005 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |
| WO | 2008/107905 A2 | 9/2008 |
| WO | 2009/009799 A1 | 1/2009 |
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2011/06886 A2 | 1/2011 |
| WO | 2011/038048 A1 | 3/2011 |
| WO | 2011/081688 A1 | 7/2011 |
| WO | 2012/003369 A2 | 1/2012 |
| WO | 2012/061935 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2014/109879 A1 | 7/2014 |

OTHER PUBLICATIONS

International Search Report and Written Opinion dated Nov. 2, 2012, for International Patent Application No. PCT/US12/53168, filed Aug. 30, 2013 (8 pages).

International Search Report and Written Opinion dated Apr. 14, 2014, for International Patent Application No. PCT/US2013/076148, filed Dec. 18, 2013 (8 pages).

International Search Report and Written Opinion dated Apr. 21, 2014, for International Patent Application No. PCT/US2013/076015, filed Dec. 18, 2013 (7 pages).

International Search Report and Written Opinion dated Apr. 23, 2014, for International Patent Application No. PCT/US2013/075328, filed Dec. 16, 2013 (8 pages).

International Search Report and Written Opinion dated Apr. 29, 2014, for International Patent Application No. PCT/US13/76093, filed Dec. 18, 2013 (6 pages).

International Search Report and Written Opinion dated Apr. 9, 2014, for International Patent Application No. PCT/US13/75089, filed Dec. 13, 2013 (7 pages).

International Search Report and Written Opinion dated Feb. 21, 2014, for International Patent Application No. PCT/US13/76053, filed Dec. 18, 2013 (9 pages).

International Search Report and Written Opinion dated Feb. 21, 2014, for International Patent Application No. PCT/US2013/076965, filed Dec. 20, 2013 (8 pages).

International Search Report and Written Opinion dated Feb. 27, 2014, for International Patent Application No. PCT/US13/75416, filed Dec. 16, 2013 (7 pages).

International Search Report and Written Opinion dated Feb. 28, 2014, for International Patent Application No. PCT/US13/75653, filed Dec. 17, 2013 (7 pages).

International Search Report and Written Opinion dated Feb. 28, 2014, for International Patent Application No. PCT/US13/75990, filed Dec. 18, 2013 (7 pages).

International Search Report and Written Opinion dated Jan. 16, 2009, for International Patent Application No. PCT/US08/78963 filed on Oct. 6, 2008 (7 Pages).

International Search Report and Written Opinion dated Jul. 30, 2014, for International Patent Application No. PCT/US14/21659, filed Mar. 7, 2014 (15 pages).

International Search Report and Written Opinion dated Mar. 10, 2014, for International Patent Application No. PCT/US2013/076212, filed Dec. 18, 2013 (8 pages).

International Search Report and Written Opinion dated Mar. 11, 2014, for International Patent Application No. PCT/US13/76173, filed Dec. 16, 2013 (9 pages).

International Search Report and Written Opinion dated Mar. 11, 2014, for International Patent Application No. PCT/US13/76449, filed Dec. 19, 2013 (9 pages).

International Search Report and Written Opinion dated Mar. 18, 2014, for International Patent Application No. PCT/US2013/076502, filed Dec. 19, 2013 (7 pages).

International Search Report and Written Opinion dated Mar. 18, 2014, for International Patent Application No. PCT/US2013/076788, filed Dec. 20, 2013 (7 pages).

International Search Report and Written Opinion dated Mar. 19, 2014, for International Patent Application No. PCT/US13/75349, filed Dec. 16, 2013 (10 pages).

International Search Report and Written Opinion dated Mar. 19, 2014, for International Patent Application No. PCT/US2013/076587, filed Dec. 19, 2013 (10 pages).

International Search Report and Written Opinion dated Mar. 19, 2014, for International Patent Application No. PCT/US2013/076909, filed Dec. 20, 2013 (7 pages).

International Search Report and Written Opinion dated Mar. 7, 2014, for International Patent Application No. PCT/US2013/076304, filed Dec. 18, 2013 (9 pages).

International Search Report and Written Opinion dated Mar. 7, 2014, for International Patent Application No. PCT/US2013/076480, filed Dec. 19, 2013 (8 pages).

(56) References Cited

OTHER PUBLICATIONS

International Search Report and Written Opinion dated Mar. 7, 2014, for International Patent Application No. PCT/US2013/076512, filed Dec. 19, 2013 (8 pages).
International Search Report and Written Opinion dated Mar. 7, 2014, for International Patent Application No. PCT/US2013/076531, filed Dec. 19, 2013 (10 pages).
Jakobovils et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatls et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisolmpic Tissues Measured with Enhanced Polarization Sensitive Optical Coherence Tomography, Opties Express 13(12):4507-4518.
Kersey et al., 1991, Polarization Insensitive fiber optic Michelson Interferometer, Electron. Lett. 27:518-520.
Kheir et al., 2012, Oxygen Gas-Filled Microparticles Provide Intravenous Oxygen Delivery, Science Translational Medlclne 4(140):140ra88 (10 pages).
Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas. Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Comnary Compuied Tomographic Angiograms, J Am Coll Cardiol 58(19):1989-1997.
Kozbor et al., 1984, A human hybrid myeloma for production of human monoclonal antibodies, J. Immunol., 133:3001-3005.
Kruth et al., 2003, Lasers and materials In selective laser sintering, Assembly Automation, 23(4):357-371.
Kumagai et al., 1994, Ablation of polymer films by a femtosecond high-peak-power Ti:sapphire laser at 798 nm, Appliec Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.

Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barrett's Esophagus, Endoscopy, 32(12):921-930.
Little et al., 1991, The underlying coronary lesion in myocardial infarction:implicatians for coronary angiography, Clinica Cardiology, 14(11):868-874.
Loo, 2004, Nanoshell Enabled Photoniu-Based Imaging and Therapy of Cancer, Technology in Cancer Research & Treatment 3(1):33-40.
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antlbodies: filamentous phage displaylng antibody variable domains, Nature 348:552-554.
Mendieta et al., 1996, Complementary sequence correlations with applications to reflectometry studies, Instrumentation and Development 3(6):37-46.
Mickley, 2008, Steal Syndrome-strategies to preserve vascular access and extremity, Nephrol Dial Transplant 23:19-24.
Miller et al., 2010. The MILLER banding pmoedure is an effective method for treating dialysis-associated steal syndrome. Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.
Morrison et al., 1984, Chimeric human antibody molecules: mouse antigen-binding domains with human constant ragion domains, PNAS 81:8851-6855.
Munson et al., 1980, Ligand: a versatile computerized approach for characterization of ligand-binding systems, Analytical Biochemistry, 107:220-239.
Nezam, 2008, High Speed Polygon-Scanner-Based Wavelength-Swept Laser Source in the Telescope-Less Configurations with Application in Optical Coherence Tomography, Optics Letters 33(15):1741-1743.
Nissen, 2001, Coronary Angiography and Intravascular Ultrasound, American Journal of Cardiology, 87(suppl):15A-20A.
Nitenberg et al., 1995, Coronary vascular reserve in humans: a critical review of methods of evaluation and of Interpretation of the results, Eur Heart J. 16(Suppl 1):7-21.
Notice of Reason(s) for Refusal dated Apr. 30, 2013, for Japanese Patent Application No. 2011-508677 for Optical Imaging Catheter For Aberation Balancing to Volcano Corporation, which application is a Japanese national stage entry of PCT/US2009/043181 with international filing date May 7, 2009, of the same title. published on Nov. 12, 2009, as WO 2009/137704, and accompanying English translation of the Notice of Reason(s) for Refusal and machine translations of JP11-56786 and JP2004-290548 (56 pages).
Nygren, 1982, Conjugation of horseradish peroxidase to Fab fragments with different homobifunctional and heterobifunctional cross-linking reagents. A comparative study, J. Histochem. and Cytochem. 30:407-412.
Oesterle et al., 1986, Angioplasty at coronary bifurcations: single-guide, two-wire technique, Cathet Cardiovasc Diagn., 12:57-63.
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.

(56) References Cited

OTHER PUBLICATIONS

Oldenburg et al., 2003, Fast-Fourier-Domain Delay Line for In Vivo Optical Coherence Tomography with a Polygonal Scanner, Applied Optics, 42(22):4606-4611.
Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26(1):80-113.
Pain et al., 1981, Preparation of protein A-peroxidase mono conjugate using a heterobifunctional reagent, and its use in enzyme immunoassays, J Immunol Methods, 40:219-30.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultraslructural changes in genetically-altered murine skeletal muscle uslng polarization-sensitive optlcal coherence tomography, Optics Express 14(4):1547-1556.
Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation. and Scale-Invariant Image Registration, IEEE Transaction on Image Processing 5(8):1266-1271.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Robbin et al., 2002, Hemodialysls Arteriovenous Fistula Maturity: US Evaluation, Radiology 225:59-64.
Rolllns et al., 1998, In vivo video rate optical coherence tomography, Optics Express 3:219-229.
Sarunic et al., 2005, Instantaneous Complex Conjugate Resolved Spectral Domain and Swept-Source OCT Using 3x3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vase Surg. 43(2):402-405.
Sen et al., 2012, Development and validation of a new adenosine-independenl index of slenosis severity from coronary wave-intensity analysis, Journal of the American College of Cardiology 59(15):1392-1402.
Setta et al., 2005, Sort versus firm embgyo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformalics 22(21):2635-2642.
Sihan et al., 2008, A novel approach to quantitative analysis of intraluminal optical coherence tomography imaging, Comput. Cardiol:1089-1092.
Siwy et al., 2003, Electro-responsive asymmetric nanopores in polyimide with stable ion-current signal, Applied Physics A: Materials Science & Processing 76:781-785.

Smith et al., 1989, Absolute displacement measurements using modulation of the spectrum of white light in a Michelsor interferometer, Applied Optics, 28(16):3339-3342.
Smith, 1997, The Scientist and Engineer's Guide to Digital Signal Processing, California Technical Publishing, San Diego, CA:432-436.
Soller, 2003, Polarization diverse optical frequency domain interferometry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optima Express, 20(21):23414-23421.
Stenqvist et al., 1983, Stiffness of central venous catheters, Acta Anaesthesiol Sund., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamlcs of UV laser ablation of organic polymer surfaces, Journal of Applled Physics, 60(9):3315-3322.
Suzuki, 2013, A novel guidewire approach for handling acute-angle bifurcations, J lnv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2)228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Torageani et al., 2008, Evaluation of hamodialysis arteriovenous fistula maturation by color-flow Doppler ultrasound, J Vasc. Bras. 7(3):203-213.
Traunecker et al., 1991, Bispecific single chain molecules (Janusins) target cytotoxic lymphocytes on HIV infected cellsl EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18(17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et el., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-898.

(56) References Cited

OTHER PUBLICATIONS

Wang et al., 2011, In vivo intracardiac optical coherence tomograph imaging through percutaneous access: toward image-guided radio-frequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt., 11, 063001-1-063001-19.
Yasuno et al., 2004, Polarization-sensitive complex Fourier domain optical coherence tomography for Jones matrix imaging of biological samples. Applied Physics Letters 85(15):3023-3025.
Zhang et al., 2004, Full range polarization-sensitive Fourier domain optical coherence tomography, Optics Express, 12(24):6033-6039.
Zitova et al., 2003, Image registration methods: A survey. Image and Vision Computing, 21(11):977-1000.
Machine translation of JP 2000-329534.
Machine translation of JP 2004-004080.
Machine translation of JP 2000-097846.
Machine translation of JP 2000-321034.
Translation of Notice of Reason(s) for Reiusal dated Apr. 30, 2014, for Japanese Patent Application No. 2011-508677, (5 pages).
Translation of Notice of Reason(s) for Refusal dated Nov. 22, 2012, for Japanese Patent Application No. 2010-516304, (6 pages).
International Search Report dated Mar. 21, 2014 for International Application No. PCT/US13/63522 filed Oct. 4, 2013 (5 pages).
Translation of Notice of Reason(s) for Refusal dated May 25, 2012, for Japanese Patent Application No. 2009-536425, (3 pages).
Abdi et al., 2010, Principal component analysis, Wiley Interdisciplinary Reviews: Computational Statistics 2:433-459.
Adler et al., 2007, Phase-Sensitive Optical Coherence Tomography at up to 370,000 Lines Per Second Using Buffered Fourier Domain Mode-Locked Lasers, Optics Letters, 32(6):626-628.
Agresti, 1996, Models for Matched Pairs, Chapter 8, An Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"-Fast optical analysis in volume scatterers by short coherence Interferometry, Optics Letters 21(14):1087-1089.
Bain, 2011, Privacy protection and face recognition, Chapter 3, Handbook of Face Recognition, Stan et al., Springer-Verlag.
Bamea et al., 1972, A class of algorithms for fast digital image registration, IEEE Trans. Computers, 21(2):179-186.
Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation. University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.

Brown, 1992, A survey of image registration techniques, ACM Computing Surveys 24(4):325-376.
Bruining et al., 2009, Intravascular Ultrasound Registration/Integration with Coronary Angiography, Cardiology Clinics, 27(3):531-540.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty. Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve In risk prediction, Circulation 115(7):928-35.
D'Agostino et al., 2001, Validation of the Framingham coronary heart disease prediction score: results of a multiple ethnic group Investigation, JAMA 286:180-187.
David et al., 1974, Protein iodination with solid-state lactaperaxidase. Biochemistry 13:1014-1021.
Davies et al., 1985, Plaque fissuring-the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?" http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles. Science, 277(5329):1078-1080.
Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barnett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61(1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radio-frequency ablation lesion formation using an optical coherence tomography forward-imaging catheter, Journal of Biomedical Optics 15 (3):030516-1 (3 pages).
Fookes et al., 2002, Rigid and non-rigid image registration and its association with mutual information:A review, Technical Report ISBN:1 86435 569 7, RCCVA, QUT.

(56) References Cited

OTHER PUBLICATIONS

Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome. Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data.logs, odds, ratios and ROC curves, Curr Opln HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion dated Mar. 11, 2014, for International Patent Application No. PCT/US13/75675, filed Dec. 17, 2013 (7 pages).
International Search Report and Written Opinion dated Mar. 19, 2014, for International Patent Application No. PCT/US13/075353, filed Dec. 16, 2013 (8 pages).

\* cited by examiner

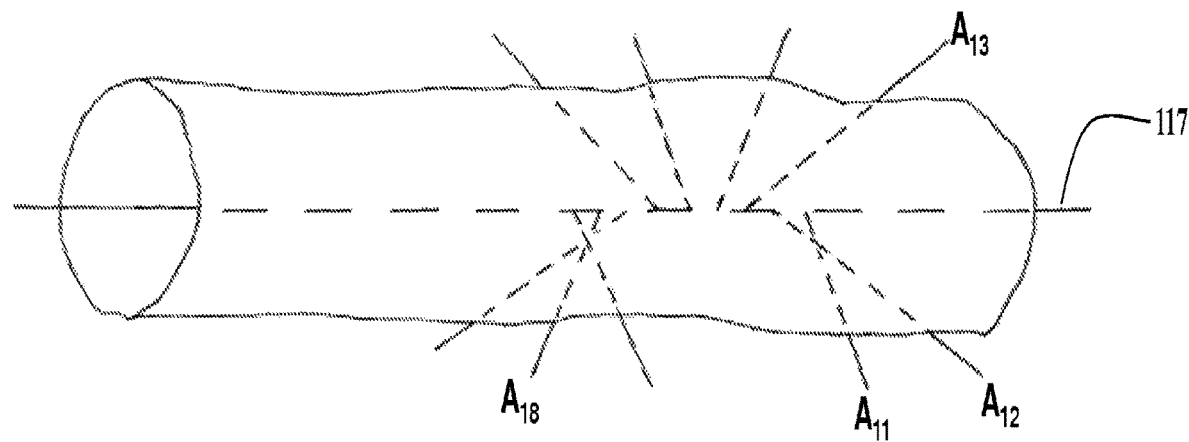
FIG. 9
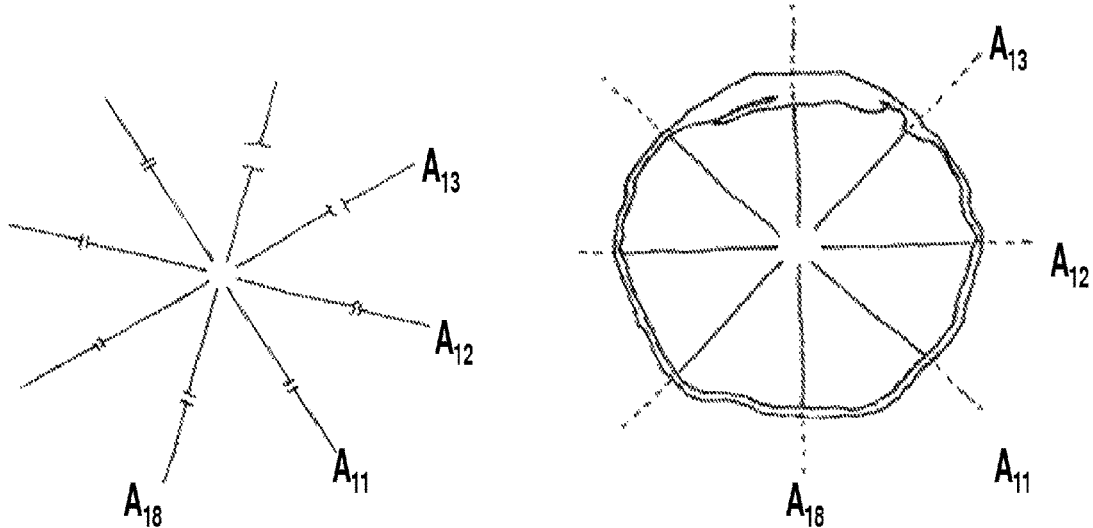
FIG. 10
FIG. 11

SYSTEMS FOR INDICATING PARAMETERS IN AN IMAGING DATA SET AND METHODS OF USE

STATEMENT OF RELATED APPLICATIONS

This application is a continuation of U.S. application Ser. No. 14/044,987, filed Oct. 3, 2013, now U.S. Pat. No. 10,568,586, which claims priority to U.S. Provisional Patent Application No. 61/710,419, filed Oct. 5, 2012, each of which is incorporated herein by reference in their entirety.

FIELD OF THE INVENTION

The invention generally relates to systems for indicating parameters in an imaging data set, for example, an imaging data set relating to a medical device or a biological lumen.

BACKGROUND

Tomographic imaging is a signal acquisition and processing technology that allows for high-resolution cross-sectional imaging in biological systems. Tomographic imaging systems include, for example, optical coherence tomography systems, ultrasound imaging systems, and computed tomography. Tomographic imaging is particularly well-suited for imaging the subsurface of a vessel or lumen within the body, such as a blood vessel, using probes disposed within a catheter through a minimally invasive procedure.

Typical tomographic imaging catheters consist of an imaging core that rotates and moves longitudinally through a blood vessel, while recording an image video loop of the vessel. The motion results in a 3D dataset, where each frame provides a 360 degree slice of the vessel at different longitudinal section. These frames provide cardiologists with invaluable information such as the location and severity of the stenosis in a patient, the presence of vulnerable plaques, and changes in cardiovascular disease over time. The information also assists in determining the appropriate treatment plan for the patient, such as drug therapy, stent placement, angioplasty, bypass surgery, valve replacement, etc.

Generally, to graphically analyze tomographic images, a clinician scrolls through a series of image frames and manually performs various measurements on the anatomical structure of interest. In some instances, a computational algorithm is also used to calculate various anatomical measurements and display their numerical values to an image display screen. While the numerical output provides useful information, it is time consuming to evaluate and compare a large data set of tomographic images by scrolling through frames of images. The extended periods of scrutiny also lead to mental fatigue, and in turn, may lead to observer error.

In addition to evaluating vasculature, tomographic imagining may also be used to place or evaluate vascular stents. A stent is a small, tube-like structure made of a metal or polymer that is inserted into a blood vessel to hold the vessel open and keep it from occluding blood flow. A stent can also be used to reinforce an area of a vessel where the wall tissues are thin or calcification has formed. Typically, a stent is placed with a balloon catheter after the vessel has been imaged.

There are several risks associated with stent placement, however. For example, the stent can cause vascular lesions that may later embolize (dislodge and block vasculature). To avoid lesions, the stent should be placed in parallel within the vessel and the stent should uniformly contact the vessel wall during deployment. Additionally, it is critical that there is no dead space between the stent and the vessel wall because of a risk of a subsequent blockage or thrombus because of blood pooling or clotting between the stent and the vessel wall. (A stent that has been placed with gaps between the stent and the vessel wall is said to be in "incomplete apposition.") Therefore, it is critical to verify that the stent is properly placed.

When tomographic imaging is used to evaluate a stent (or other medical device) many of the same issues arise with respect to overwhelming sets of images and fatigue related to processing the images. In addition, it can be difficult to immediately discern problematic placement of a medical device because of the visual similarity between a properly and improperly placed device when the images are displayed on a computer monitor, for example.

SUMMARY OF THE INVENTION

The invention generally provides systems and methods for helping health care providers visualize important parameters in a medical image. The user is provided with an enhanced graphical display of images defining biological lumens and/or medical devices resulting from anatomical measurements. A variety of important parameters can be emphasized through the use of visual, audio, or tactile displays or alerts. In some instances, the imaging data sets will have been obtained from optical coherence tomography or ultrasound measurements. For even greater analysis, interaction with the images will prompt the display of additional, relevant images with greater detail. Accordingly, methods of the invention will speed review of the image data sets by allowing a provider to more quickly synthesize the data and focus on areas of concern. Additionally, displaying images with relevant indicators and the use of alerts will reduce the potential for error during clinical evaluation.

The invention includes systems and methods for aiding a user in analyzing an imaging data set relating to a medical device and a biological structure defining a lumen. The system comprises a monitor to display an image, a central processing unit (CPU), and storage coupled to the CPU for storing instructions to carry out the methods of the invention. Typically, the instructions configure the CPU to analyze the imaging data set for a parameter, assign an indicator to the medical device based on the presence of the parameter, and display the indicator. In some embodiments, the indicator is a color. The parameter may relate to any of a number of conditions or concerns that could be evaluated with the information contained in the imaging data set. For example, the parameter might be diameter of a vessel, area of a vessel lumen, thickness of a vessel lumen wall, plaque burden, vessel remodeling index, tissue type, size of a thrombus, location of a thrombus, blood flow, blood pressure, fluid dynamic measurement, stent type, stent apposition, stent coverage, stent fracture, or stent placement. The medical device may be a stent, a pacemaker, a prosthetic valve, a graft, and implant, a sterilization device, a catheter, or an electrode.

The invention is applicable to imaging data sets from devices that produce two dimensional data sets from which three dimensional image compositions are derived, for example optical coherence tomography, intravascular ultrasound, co-registered optical coherence tomography and intravascular ultrasound, co-registered optical coherence tomography and angioscopy, co-registered intravascular ultrasound and angioscopy, spectroscopy, photoacoustic tomography, intravascular magnetic resonance imaging, angioscopy, or combinations thereof.

The invention additionally includes systems and methods to aid a user in assessing an imaging data set relating to a lumen of a biological structure. The system comprises a monitor to display an image, a central processing unit (CPU), and storage coupled to the CPU for storing instructions to carry out the methods of the invention. Typically, the instructions configure the CPU to analyze the imaging data set for a parameter, display an image associated with the imaging data set on the monitor, provide the user with a graphical user interface (GUI) on the monitor, and activate an alert when the user interacts with the displayed image or a portion of the displayed image and the parameter is at or beyond a threshold value. The alert may be a visual alert, an audio alert, a haptic alert, a dynamic gauge indicator alert, or a combination thereof. In some embodiments the visual alert is a color-coded indicator, a pulsating indicator, a color map of the image parameter, an altered-sized image, an altered-sized parameter encoded in an image, a gauge, a callout marker, or combinations thereof. In some embodiments, the user is provided with a dynamic graphical icon based on the parameter.

In other aspects the instructions may configure the CPU to analyze the imaging data set for a plurality of values of a parameter, display on the monitor a first intraluminal image having indicators corresponding to the values of the parameter, provide the user with a graphical user interface (GUI) on the monitor, and display a value of the parameter when the user interacts with the intraluminal image. Alternatively or additionally, when the user interacts with the first intraluminal image the system may display a second intraluminal image. In an embodiment, the first intraluminal image is a 3D representation of a lumen and the second intraluminal image is a cross-sectional view of the lumen.

BRIEF DESCRIPTION OF FIGURES

FIG. 9 shows the positioning of A-scans within a vessel.

FIG. 10 illustrates a set of A-scans used to compose a B-scan according to certain embodiments of the invention.

FIG. 11 shows the set of A-scans shown in FIG. 10 within a cross section of a vessel.

DESCRIPTION OF THE INVENTION

Figure 1:
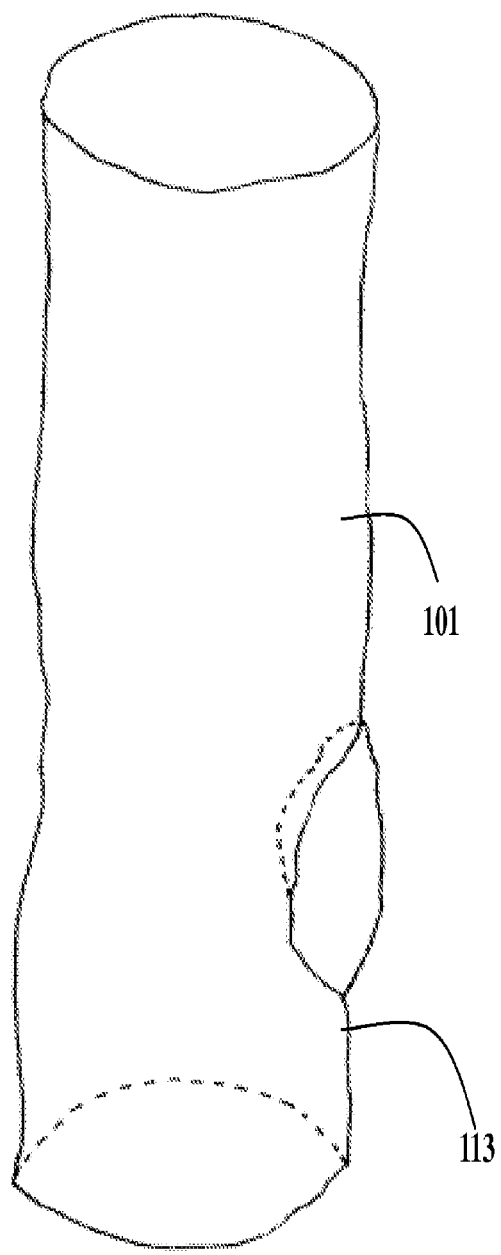
FIG. 1 is a perspective view of a vessel.

This invention generally relates to systems for indicating parameters in an imaging data set, for example, an imaging data set relating to a medical device or a biological lumen. Medical imaging is a general technology class in which sectional and multidimensional anatomic images are constructed from acquired data. The data can be collected from a variety of signal acquisition systems including, but not limited to, magnetic resonance imaging (MRI), radiography methods including fluoroscopy, x-ray tomography, computed axial tomography and computed tomography, nuclear medicine techniques such as scintigraphy, positron emission tomography and single photon emission computed tomography, photo acoustic imaging ultrasound devices and methods including, but not limited to, intravascular ultrasound spectroscopy (IVUS), ultrasound modulated optical tomography, ultrasound transmission tomography, other tomographic techniques such as electrical capacitance, magnetic induction, functional MRI, optical projection and thermoacoustic imaging, combinations thereof and combinations with other medical techniques that produce one-, two- and three-dimensional images. Although the exemplifications described herein are drawn to the invention as applied to OCT, at least all of these techniques are contemplated for use with the systems and methods of the present invention.

Through the use of the imaging techniques described herein, anatomical structures can be evaluated, visually optimized, or linked to at least one other sensory output when a predetermined threshold is reached, and provided to the user. Corresponding numerical measurements can be provided to the user by these methods in one-, two- or three-dimensional image data sets. User interface graphics also may provide input for other indicators on a monitor interface, for example a color bar associated with percent changes in size, depth, height, width, etc., of an anatomical structure or dynamic graphical indicators displaying a value correlated to a lumen image parameter. The method enhances visual examination each image in image data sets, thereby reducing user error in evaluation and assessment of a clinical condition.

The methods and systems of the present invention embody various visual, audio, or tactile indicators to emphasize image parameters in medical images. Such indicators include, for example, a color-coded indicator, a pulsating indicator, a color map of the image parameter, an altered-sized lumen image, an altered-sized parameter encoded in a lumen image, a gauge, a callout marker, and combinations thereof. In certain embodiments, the pulsating indicator can be an icon, a lumen image, a lumen image parameter, a color-coded indicator, a color map of the image parameter, and any combination. In other examples, the pulsating of the pulsating indicator occurs at a frequency specific to the image parameter. In some embodiments, a heat map of image parameters may be used, such that a user may quickly assess a plurality of values of a parameter. For example a structure may be coded red to green based upon low to high, or bad to good, or high risk to low risk, to indicate a range of values. Alternatively, structures may also be coded with shading or fill designs (e.g., cross-hatching) to indicate values of parameters.

Various embodiments of visual indicators can include, for example, a dynamic graphical icon for the image parameter. The dynamic graphical icon can be a callout marker that brackets or otherwise delimits a parameter as a user scrolls through a series of images, or it can be, for example, a needle gauge that adjusts its value to any of a range of values for an image parameter that changes as a user scrolls through a set of images.

The systems and methods described herein are not limited to the display of a single parameter, however. That is, in some embodiments, multiple parameters are simultaneously displayed. Each parameter may have a corresponding visual, audio, or haptic indicator. In some embodiments, multiple parameters are indicated by multiple color schemes. In some embodiments, multiple parameters are indicated by a mix of visual, audio, and haptic indicators. In some embodiments, a user may toggle between parameters or the user will see a second image indicating a different parameter as the user interacts with the image.

Other examples of the present invention include an indicator that is activated as a user scrolls over at least one image having a predetermined parameter threshold. A sensory inducing output can include, for example, a visual indicator, an audio indicator, a haptic indicator, a gauge indicator, and combinations thereof. In certain examples, the visual sensory inducing output can include a color-coded indicator, a pulsating indicator, a color map of the image parameter, an altered-sized lumen image, an altered-sized parameter encoded in a lumen image, and combinations thereof. Alternatively, the background of the image could flash, the screen could momentarily show a negative image of the displayed image and then return, or a color image could change to a half-tone image.

The pulsating indicator may be, for example, an icon, a lumen image, a lumen image parameter, a color-coded indicator, a color map of the image parameter, or any combination thereof. An image may pulsate at a rate related to the parameter of interest. Generally, any indicator can be set to occur once a threshold value of a parameter is reached.

Audio indicators may include, for example, a sound specific to a parameter. In certain embodiments, the audio indicator can become activated if an image parameter is present in any particular image. In other embodiments, the audio indicator can become activated when, for example, a user scrolls over a lumen image encoding a threshold value of a particular image parameter. The audio indicator may be a tone, beep, music (e.g., musical scale), horn, or a buzz.

In other examples, a sensory inducing output includes haptic indicators, for example a vibration in a system component at a physical interface between a user and the system component. The system component can include, as non-limiting examples, a computer-aided display control module, hereinafter referred to as a "computer mouse," or a touch-screen monitor that imparts a tactile signal to the user, for example a vibration, as a user scrolls over a lumen image encoding a threshold value of a particular image parameter. In related embodiments, a haptic indicator can be activated if a particular image encodes the desired parameter, or an image parameter threshold is encoded in the image.

Figure 2:
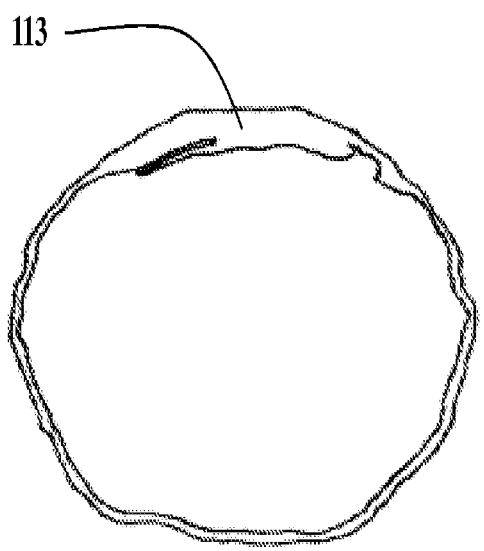
FIG. 2 is a cross-sectional view of the vessel shown in FIG. 1.

Systems and methods of the invention have application in intravascular imaging methodologies such as intravascular ultrasound (IVUS) and optical coherence tomography (OCT) among others that produce a three-dimensional image of a lumen. A segment of a lumen 101 is shown in FIG. 1 in a 3D-view having a feature 113 of interest. FIG. 2 shows a cross-section of lumen 101 through feature 113. In certain embodiments, intravascular imaging involves positioning an imaging device near feature 113 and collecting data representing a three-dimensional image.

Various lumens of biological structures may be imaged with the described technologies, including blood vessels, vasculature of the lymphatic and nervous systems, various structures of the gastrointestinal tract including lumen of the small intestine, large intestine, stomach, esophagus, colon, pancreatic duct, bile duct, hepatic duct, lumen of the reproductive tract including the vas deferens, vagina, uterus and fallopian tubes, structures of the urinary tract including urinary collecting ducts, renal tubules, ureter, and bladder, and structures of the head and neck and pulmonary system including sinuses, parotid, trachea, bronchi, and lungs.

The arteries of the heart are particularly useful to examine with imaging devices such as OCT. OCT imaging of the coronary arteries can determine the amount of plaque built up at any particular point in the coronary artery. The accumulation of plaque within the artery wall over decades is the setup for vulnerable plaque which, in turn, leads to heart attack and stenosis (narrowing) of the artery. OCT is useful in determining both plaque volume within the wall of the artery and/or the degree of stenosis of the artery lumen. It can be especially useful in situations in which angiographic imaging is considered unreliable, such as for the lumen of ostial lesions or where angiographic images do not visualize lumen segments adequately. Example regions include those with multiple overlapping arterial segments. It is also used to assess the effects of treatments of stenosis such as with hydraulic angioplasty expansion of the artery, with or without stents, and the results of medical therapy over time. In an exemplary embodiment, the invention provides a system for capturing a three dimensional image by OCT.

OCT is a medical imaging methodology using a specially designed catheter with a miniaturized near infrared light-emitting probe attached to the distal end of the catheter. As an optical signal acquisition and processing method, it captures micrometer-resolution, three-dimensional images from within optical scattering media (e.g., biological tissue). Commercially available OCT systems are employed in diverse applications, including art conservation and diagnostic medicine, notably in ophthalmology where it can be used to obtain detailed images from within the retina. The detailed images of the retina allow one to identify several eye diseases and eye trauma. Recently it has also begun to be used in interventional cardiology to help diagnose coronary artery disease. OCT allows the application of interferometric technology to see from inside, for example, blood vessels, visualizing the endothelium (inner wall) of blood vessels in living individuals.

Other applications of OCT and other signal processing imaging systems for biomedical imaging include use in: dermatology in order to image subsurface structural and blood flow formation; dentistry in order to image the structure of teeth and gum line to identify and track de-mineralization and re-mineralization, tarter, caries, and periodontal disease; gastroenterology in order to image the gastrointestinal tract to detect polyps and inflammation, such as that caused by Crohn's disease and ulcerative colitis; cancer diagnostics in order to discriminate between malignant and normal tissue.

Generally, an OCT system comprises three components which are 1) an imaging catheter 2) OCT imaging hardware, 3) host application software. When utilized, the components are capable of obtaining OCT data, processing OCT data, and transmitting captured data to a host system. OCT systems and methods are generally described in Milner et al., U.S. Patent Application Publication No. 2011/0152771, Condit et al., U.S. Patent Application Publication No. 2010/0220334, Castella et al., U.S. Patent Application Publication No. 2009/0043191, Milner et al., U.S. Patent Application Publication No. 2008/0291463, and Kemp, N., U.S. Patent Application Publication No. 2008/0180683, the content of each of which is incorporated by reference in its entirety. In certain embodiments, systems and methods of the invention include processing hardware configured to interact with more than one different three dimensional imaging system so that the tissue imaging devices and methods described here in can be alternatively used with OCT, IVUS, or other hardware.

In OCT, a light source delivers a beam of light to an imaging device to image target tissue. Light sources can be broad spectrum light sources, or provide a more limited spectrum of wavelengths, e.g., near infra-red. The light sources may be pulsed or continuous wave. For example the light source may be a diode (e.g., superluminescent diode), or a diode array, a semiconductor laser, an ultrashort pulsed laser, or supercontinuum light source. Typically the light source is filtered and allows a user to select a wavelength of light to be amplified. Wavelengths commonly used in medical applications include near-infrared light, for example between about 800 nm and about 1700 nm. Methods of the invention apply to image data obtained from obtained from any OCT system, including OCT systems that operate in either the time domain or frequency (high definition) domain.

In time-domain OCT, an interference spectrum is obtained by moving a scanning optic, such as a reference mirror, longitudinally to change the reference path and match multiple optical paths due to reflections of the light within the sample. The signal giving the reflectivity is sampled over time, and light traveling at a specific distance creates interference in the detector. Moving the scanning mechanism laterally (or rotationally) across the sample produces reflectance distributions of the sample (i.e., an imaging data set) from which two-dimensional and three-dimensional images can be produced.

In frequency domain OCT, a light source capable of emitting a range of optical frequencies passes through an interferometer, where the interferometer combines the light returned from a sample with a reference beam of light from the same source, and the intensity of the combined light is recorded as a function of optical frequency to form an interference spectrum. A Fourier transform of the interference spectrum provides the reflectance distribution along the depth within the sample.

Several methods of frequency domain OCT are described in the literature. In spectral-domain OCT (SD-OCT), also sometimes called "Spectral Radar" (*Optics Letters*, vol. 21, No. 14 (1996) 1087-1089), a grating or prism or other means is used to disperse the output of the interferometer into its optical frequency components. The intensities of these separated components are measured using an array of optical detectors, each detector receiving an optical frequency or a fractional range of optical frequencies. The set of measurements from these optical detectors forms an interference spectrum (Smith, L. M. and C. C. Dobson, *Applied Optics* vol. 28: (1989) 3339-3342), wherein the distance to a scatterer is determined by the wavelength dependent fringe spacing within the power spectrum. SD-OCT has enabled the determination of distance and scattering intensity of multiple scatters lying along the illumination axis by analyzing the exposure of an array of optical detectors so that no scanning in depth is necessary.

Alternatively, in swept-source OCT, the interference spectrum is recorded by using a source with adjustable optical frequency, with the optical frequency of the source swept through a range of optical frequencies, and recording the interfered light intensity as a function of time during the sweep. An example of swept-source OCT is described in U.S. Pat. No. 5,321,501.

Time- and frequency-domain systems can further vary based upon the optical layout of the systems: common beam path systems and differential beam path systems. A common beam path system sends all produced light through a single optical fiber to generate a reference signal and a sample signal whereas a differential beam path system splits the produced light such that a portion of the light is directed to the sample and the other portion is directed to a reference surface. Common beam path systems are described in U.S. Pat. Nos. 7,999,938; 7,995,210; and 7,787,127 and differential beam path systems are described in U.S. Pat. Nos. 7,783,337; 6,134,003; and 6,421,164, the contents of each of which are incorporated by reference herein in their entireties.

Figure 3:
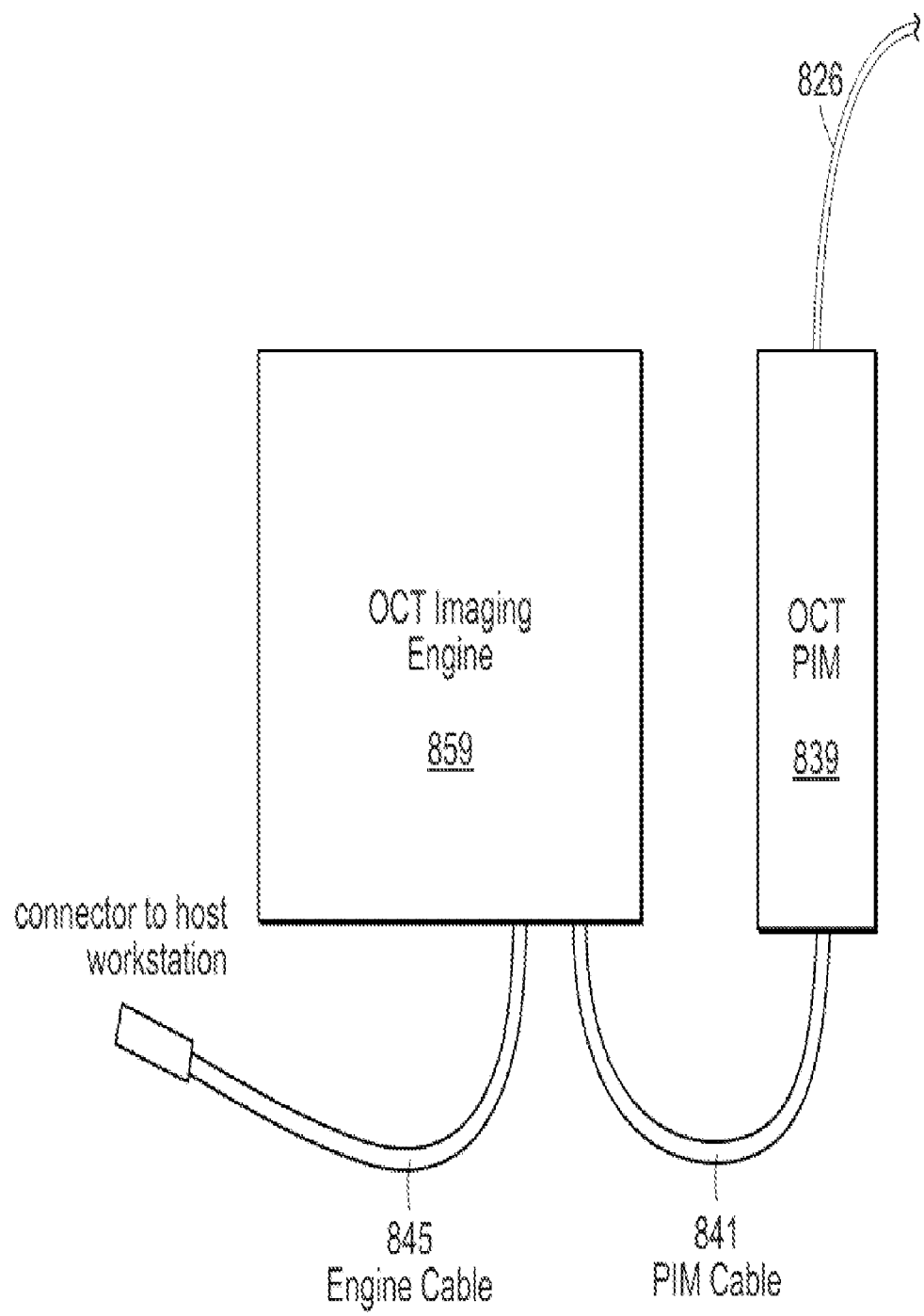
FIG. 3 is a diagram of components of an optical coherence tomography (OCT) system.

In certain embodiments, the invention provides a differential beam path OCT system with intravascular imaging capability as illustrated in FIG. 3. For intravascular imaging, a light beam is delivered to the vessel lumen via a fiber-optic based imaging catheter 826. The imaging catheter is connected through hardware to software on a host workstation. The hardware includes imagining engine 859 and a handheld patient interface module (PIM) 839 that includes user controls. The proximal end of imaging catheter 826 is connected to PIM 839, which is connected to imaging engine 859 as shown in FIG. 3.

Figure 4:
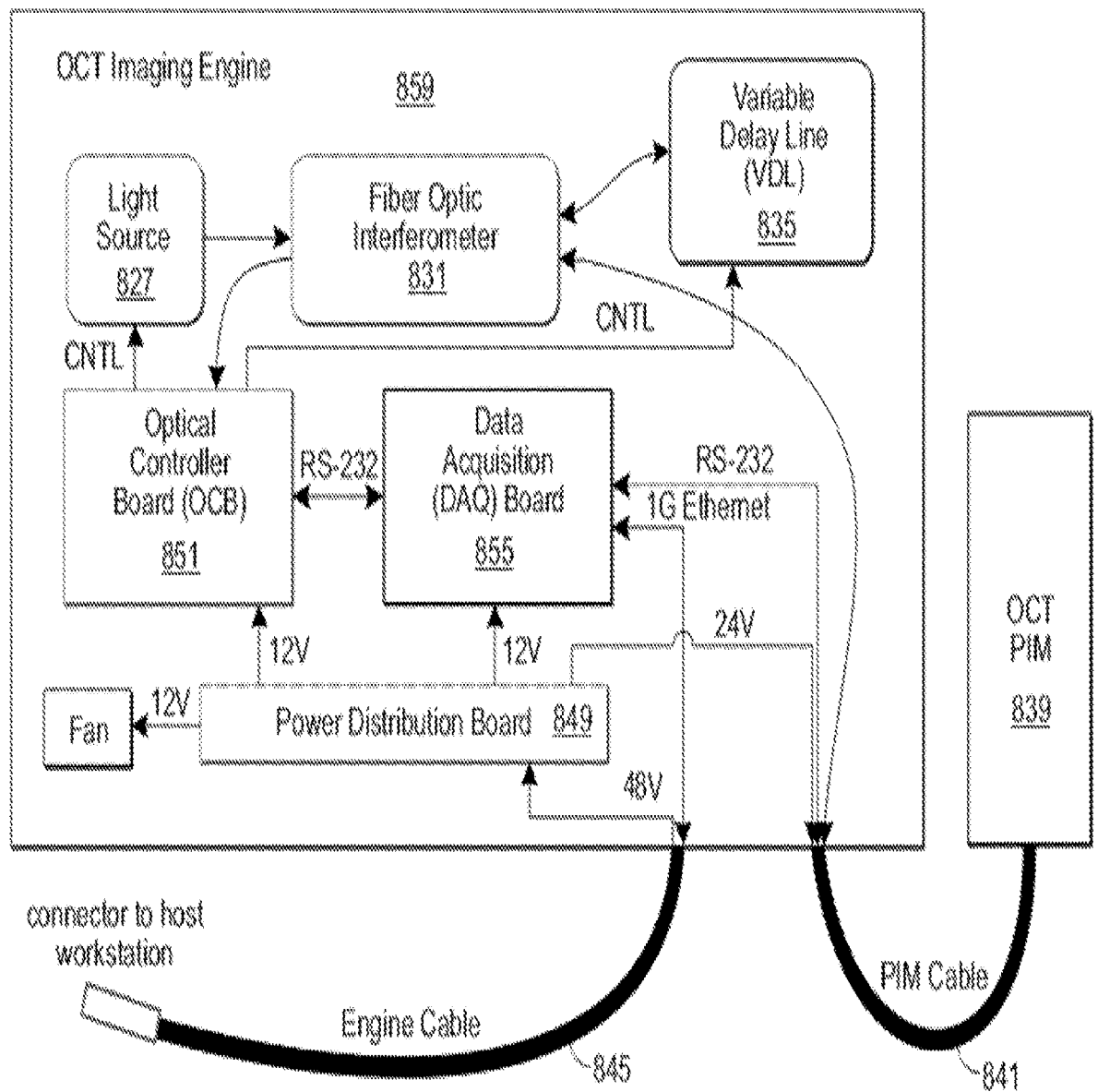
FIG. 4 is a diagram of the imaging engine shown in FIG. 3.

An embodiment of imaging engine 859 is shown in FIG. 4. Imaging engine 859 (i.e., the bedside unit) houses power distribution board 849, light source 827, interferometer 831, and variable delay line 835 as well as a data acquisition (DAQ) board 855 and optical controller board (OCB) 851. PIM cable 841 connects imagining engine 859 to PIM 839 and engine cable 845 connects imaging engine 859 to the host workstation (not shown).

Figure 5:
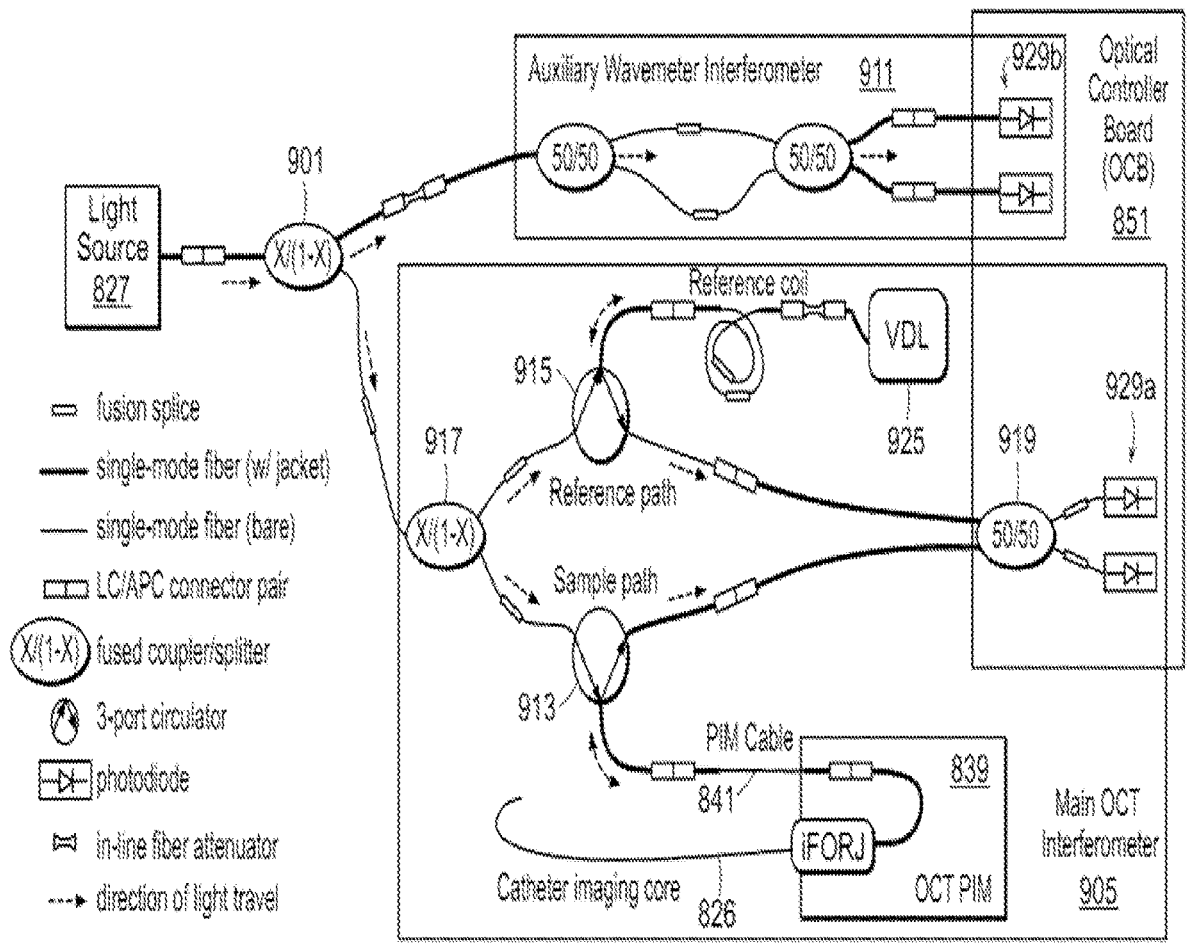
FIG. 5 is a diagram of a light path in an OCT system of certain embodiments of the invention.

FIG. 5 shows an exemplary light path in a differential beam path system which may be used in an OCT system suitable for use with the invention. Light for producing the measurements originates within light source 827. This light is split between main OCT interferometer 905 and auxiliary interferometer 911. In some embodiments, the auxiliary interferometer is referred to as a "clock" interferometer. Light directed to main OCT interferometer 905 is further split by splitter 917 and recombined by splitter 919 with an asymmetric split ratio. The majority of the light from splitter 917 is guided into sample path 913 while the remainder goes into reference path 915. Sample path 917 includes optical fibers running through PIM 839 and imaging catheter core 826 and terminating at the distal end of the imaging catheter, where the sample is measured.

The reflected light is transmitted along sample path 913 to be recombined with the light from reference path 915 at splitter 919. A variable delay line (VDL) 925 on the reference path uses an adjustable fiber coil to match the length of reference path 915 to the length of sample path 913. The reference path length is adjusted by a stepper motor translating a mirror on a translation stage under the control of firmware or software.

The combined light from splitter 919 is split into orthogonal polarization states, resulting in RF-band polarization-diverse temporal interference fringe signals. The interference fringe signals are converted to photocurrents using PIN photodiodes 929a, and 929b, on optical controller board (OCB) 851. The interfering, polarization splitting, and detection steps are done by a polarization diversity module (PDM) (not shown) on OCB 851. Signal from OCB 851 is sent to DAQ 855, shown in FIG. 4. DAQ 855 includes a digital signal processing (DSP) microprocessor and a field programmable gate array (FPGA) to digitize signals and communicate with the host workstation and PIM 839. The FPGA converts raw optical interference signals into meaningful reflectivity measurements. DAQ 855 also compresses data as necessary to reduce image transfer bandwidth, e.g., to 1 Gbps, e.g., by compressing frames with a glossy compression JPEG encoder.

Typical intravascular OCT involves introducing the imaging catheter into a patient's target vessel using standard interventional techniques and tools such as a guide wire, guide catheter, and angiography system. The imaging catheter may be integrated with IVUS by an OCT-IVUS system for concurrent imaging, as described in, for example, Castella et al. U.S. Patent Application Publication No. 2009/0043191 and Dick et al. U.S. Patent Application Publication No. 2009/0018393, both of which are incorporated by reference in their entireties.

Figure 6:
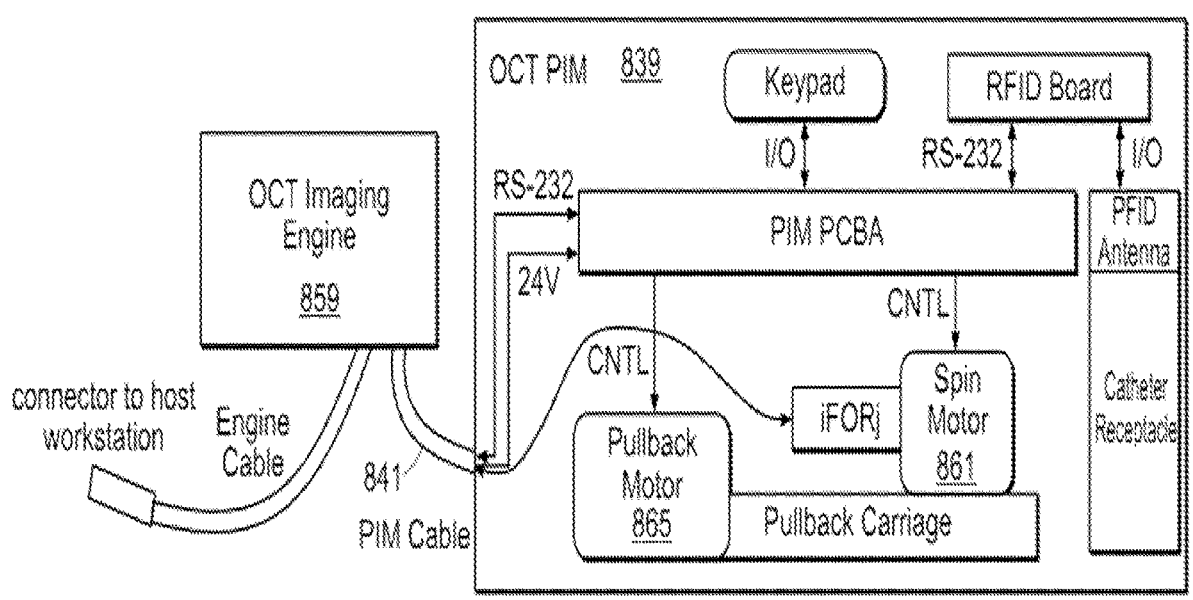
FIG. 6 is a patient interface module of an OCT system.
Figure 7:
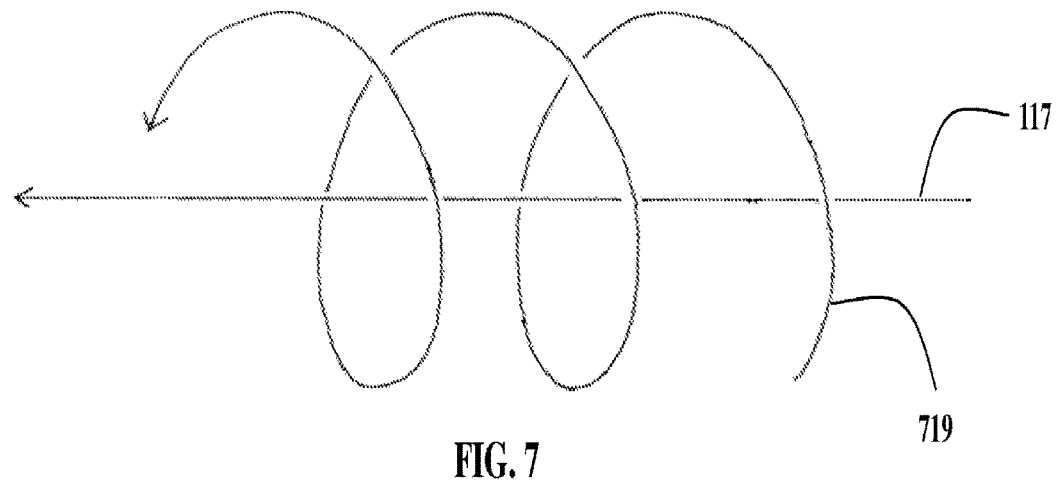
FIG. 7 is an illustration of the motion of parts of an imaging catheter according to certain embodiments of the invention.
Figure 8:
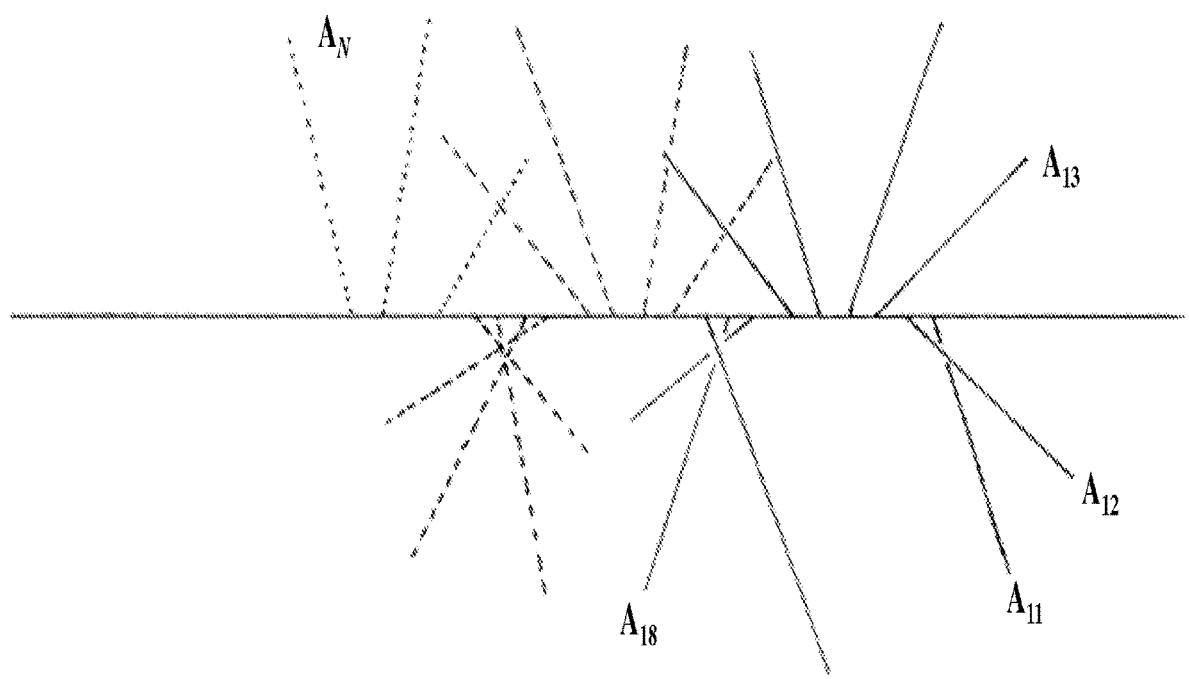
FIG. 8 shows an array of A-scan lines of a three-dimensional imaging system according to certain embodiments of the invention.

The details of PIM 839 which control the sample measurements are shown in FIG. 6. Rotation of imaging catheter core 826 is driven by spin motor 861 while proximal translation of imaging catheter core 826 is driven by pullback motor 665. The combination of rotation and translation along axis 117 produces a spiral motion for image illumination and collection, as described by FIG. 7. In many embodiments, blood within the lumen to be imaged is temporarily flushed with a clear solution prior to imaging. The reflected light is received by an inner core of imaging catheter core 826 and optically interacts with light from the reference path, giving rise to an array of reflectance distribution vectors (A-scans) as illustrated schematically in FIG. 8.

FIG. 9 shows an exemplary schematic of the positioning of A-scans within a lumen, e.g., a vessel. The separation between the A-scan lines has been exaggerated for simplicity. At each place where an A-scan, e.g., $A_{11}, A_{12}, \ldots, A_N$, intersects a surface of the lumen (e.g., a vessel wall) sample light illuminates the sample, is reflected, and a portion of the reflected light is captured. The captured reflected light then interacts with reference light and then is detected, as described above. Differences in reflections detected along each A-scan line are associated with features within the imaged lumen. Data is collected from A-scans $A_{11}, A_{12}, \ldots, A_N$ and stored in a tangible, non-transitory memory. Typically, rotational systems consist of an imaging core which rotates and pulls back (or pushes forward) while recording an image video loop. This motion results in a three dimensional dataset of two dimensional image frames, where each frame provides a 360° slice of the vessel at different longitudinal locations.

A collective set of A-scans generally corresponding to one rotation of catheter imaging core 826 around axis 117 is used to produce a B-scan. FIG. 10 illustrates a set of A-scans $A_{11}, A_{12}, \ldots, A_{18}$ used to compose a B-scan according to certain embodiments of the invention. These A-scan lines are shown as would be seen looking down axis 117 (i.e., longitudinal distance between them is not shown). While eight A-scan lines are illustrated in FIG. 10, typical OCT applications can include between 300 and 1,000 A-scan lines per B-scan (e.g., about 660).

Figure 12:
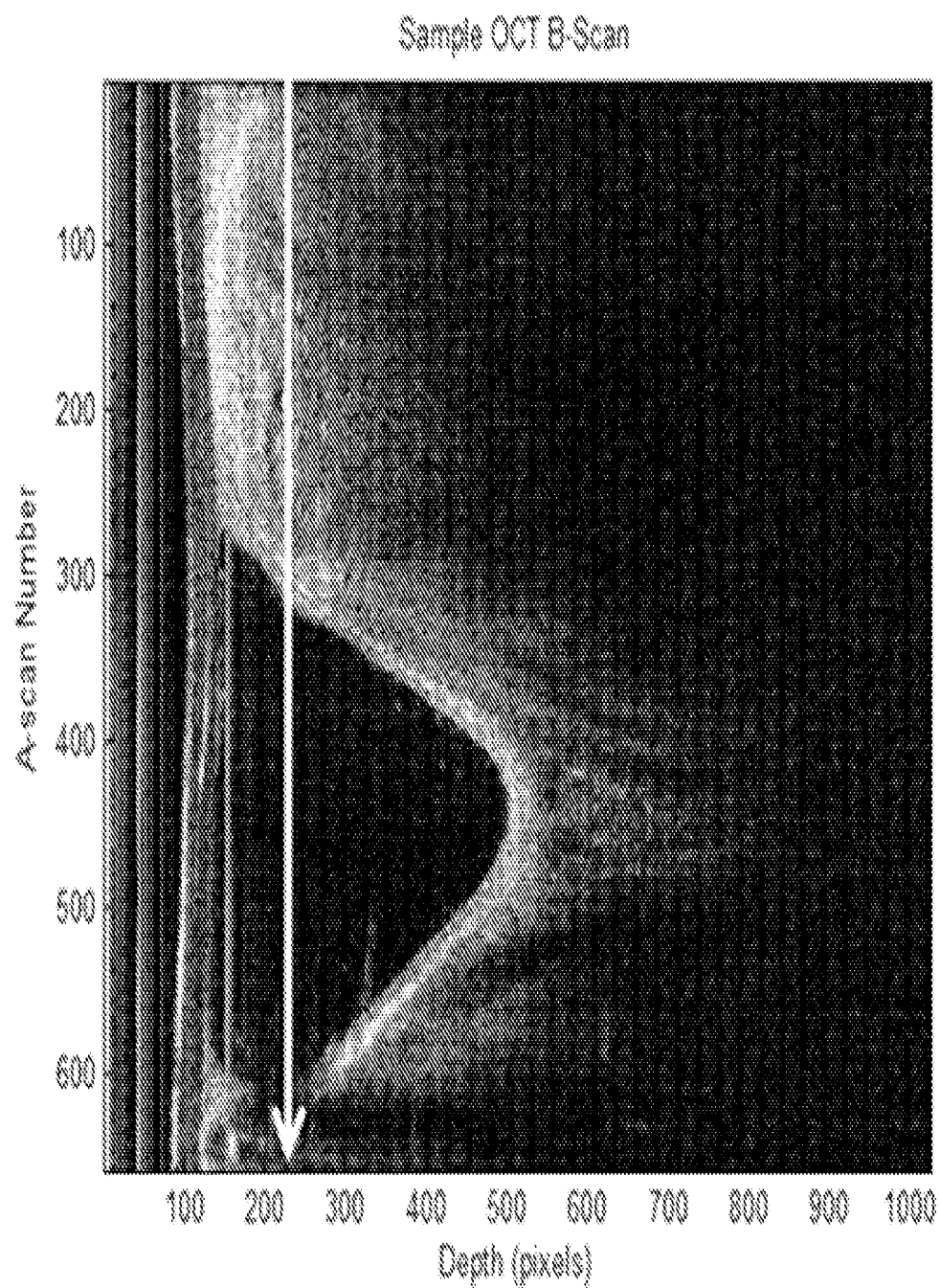
FIG. 12 shows an OCT polar coordinate B-Scan with 660 A-scans.
Figure 13:
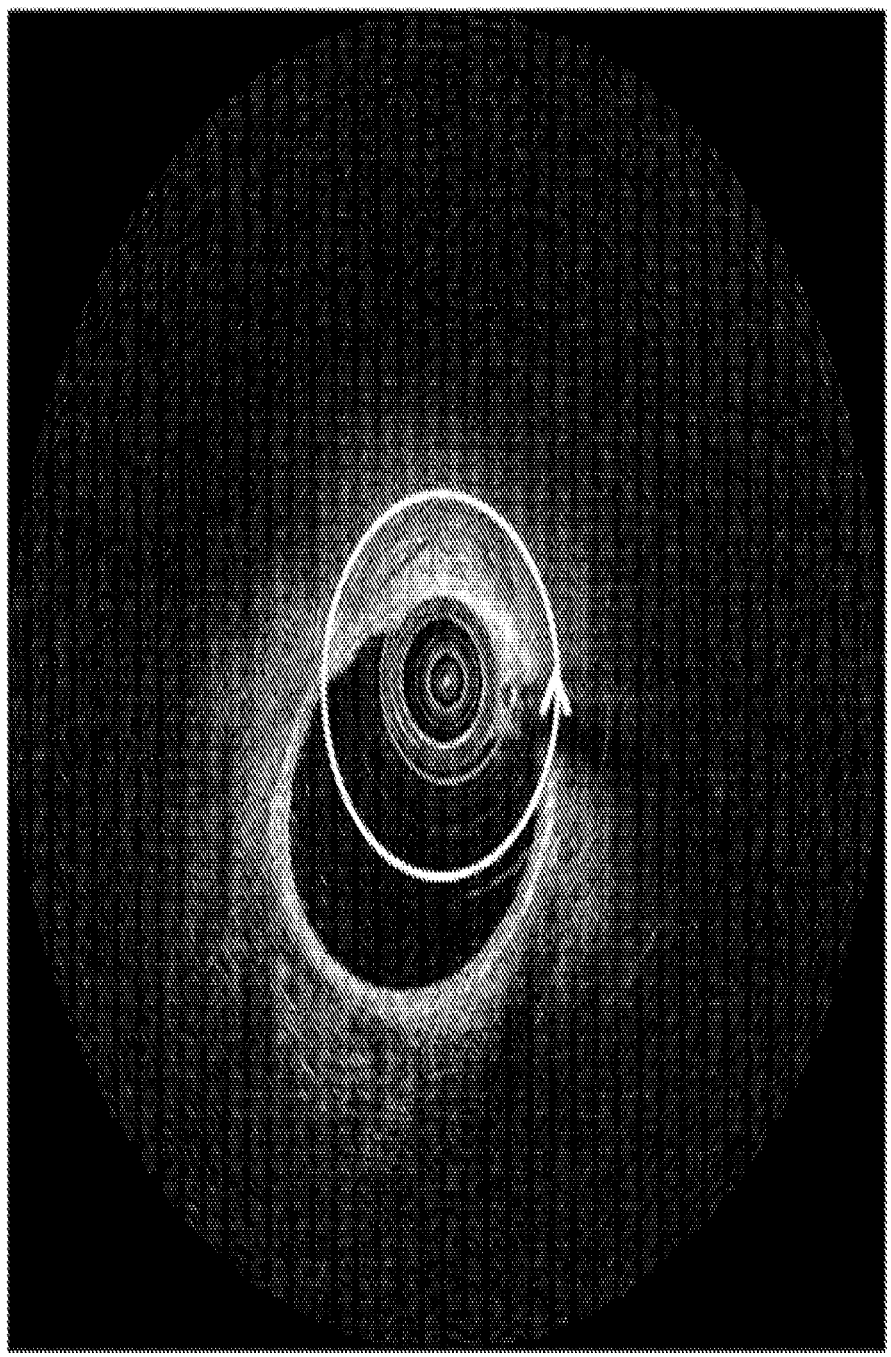
FIG. 13 shows a scan-converted image of the B-scan in FIG. 12.
Figure 22:
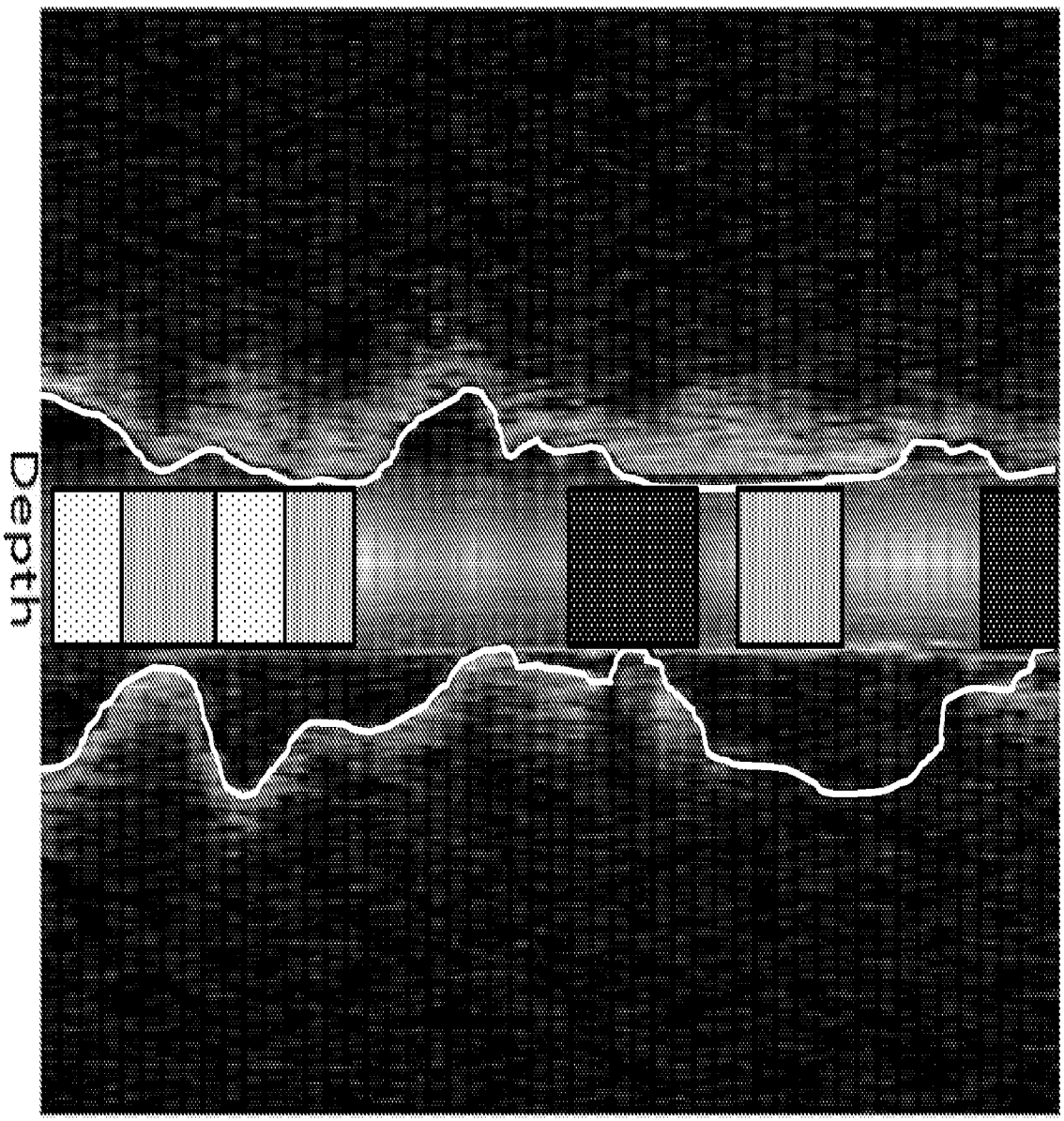
FIG. 22 illustrates a longitudinal view of a lumen with shading based upon lumen area.
Figure 23:
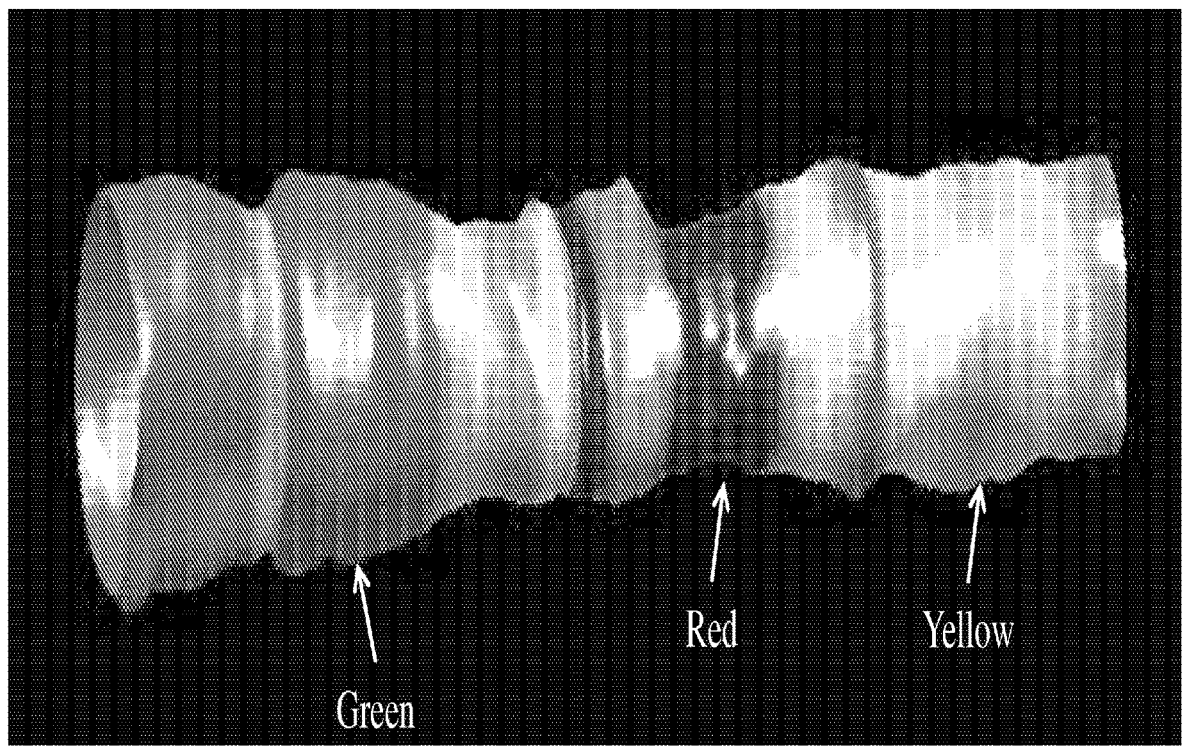
FIG. 23 illustrates a three-dimensional view of a lumen color-coded to indicate the cross sectional area.

The data of all the A-scan lines together can be used to create three-dimensional images of the tissue. First, the A-scans can be used to create a B-scan, which in one embodiment is a cross-sectional image of the lumen sometimes referred to as a tomographic view. For example, FIG. 12 shows a B-scan comprising a set of 660 A-scans collected as described in FIGS. 7-11, i.e., within a cross section of a vessel. Alternatively, the set of A-scans may be transformed by a rotational imaging modality to form a B-scan corresponding to a cross-sectional image, as shown in FIG. 13. The rotational measurement of the catheter in a counter-clockwise fashion is indicated by the circular white arrow in FIG. 13. This sampling motion corresponds to the motion of the white arrow from 0 to 660 in FIG. 12. It should also be noted in FIGS. 12-13 that the imaging catheter was closer to the upper vessel wall, leading to the concentric circles at the 12 o'clock position in FIG. 13 and a lack of symmetry FIG. 12. After B-scans are produced as a function of position along axis 117, the B-scans can be processed to produce longitudinal and three-dimensional views of the lumen, such as shown in FIGS. 22 and 23.

Figure 14:
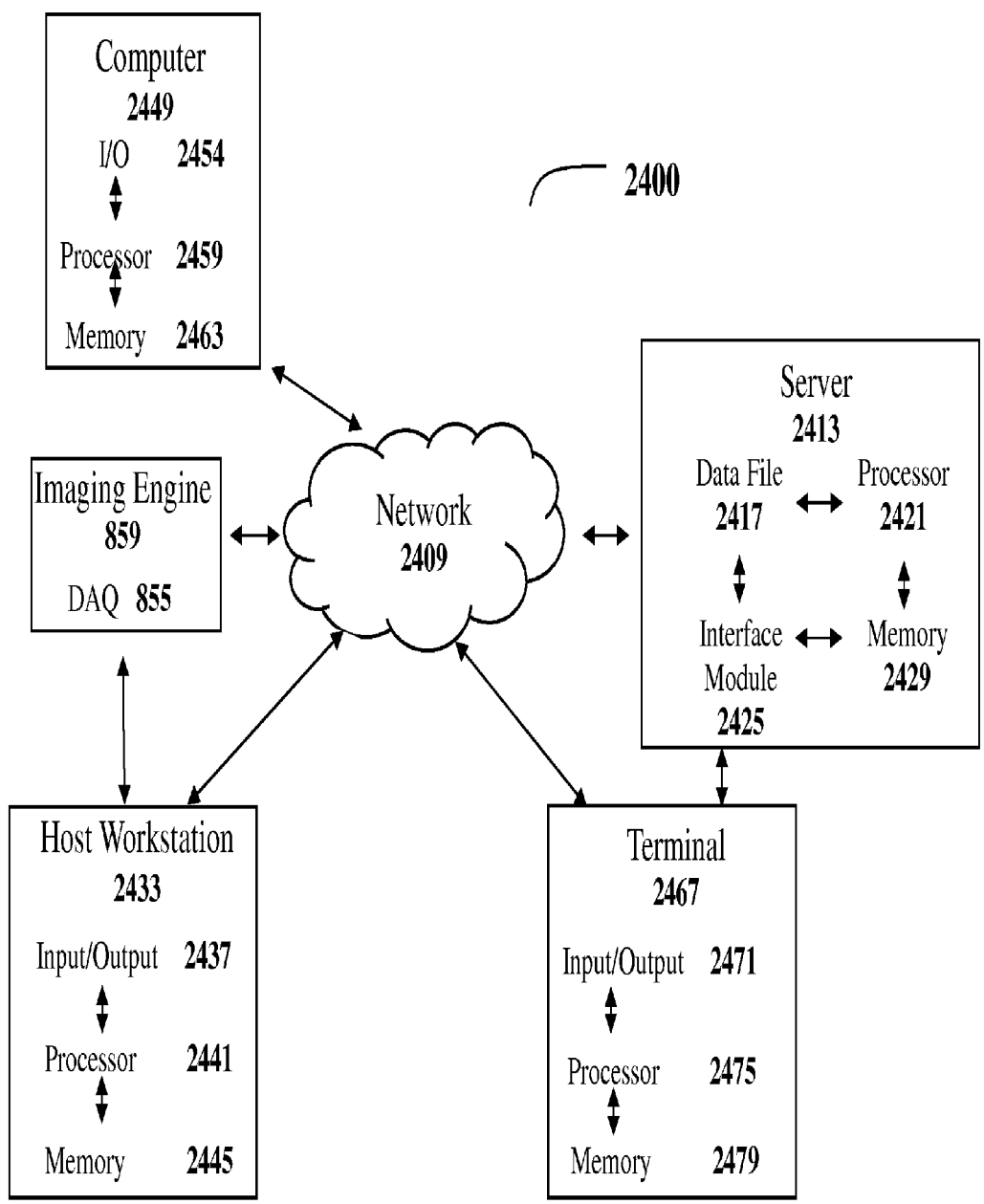
FIG. 14 is a block diagram of a system for producing images that may be processed with systems of the invention.
Figure 15:
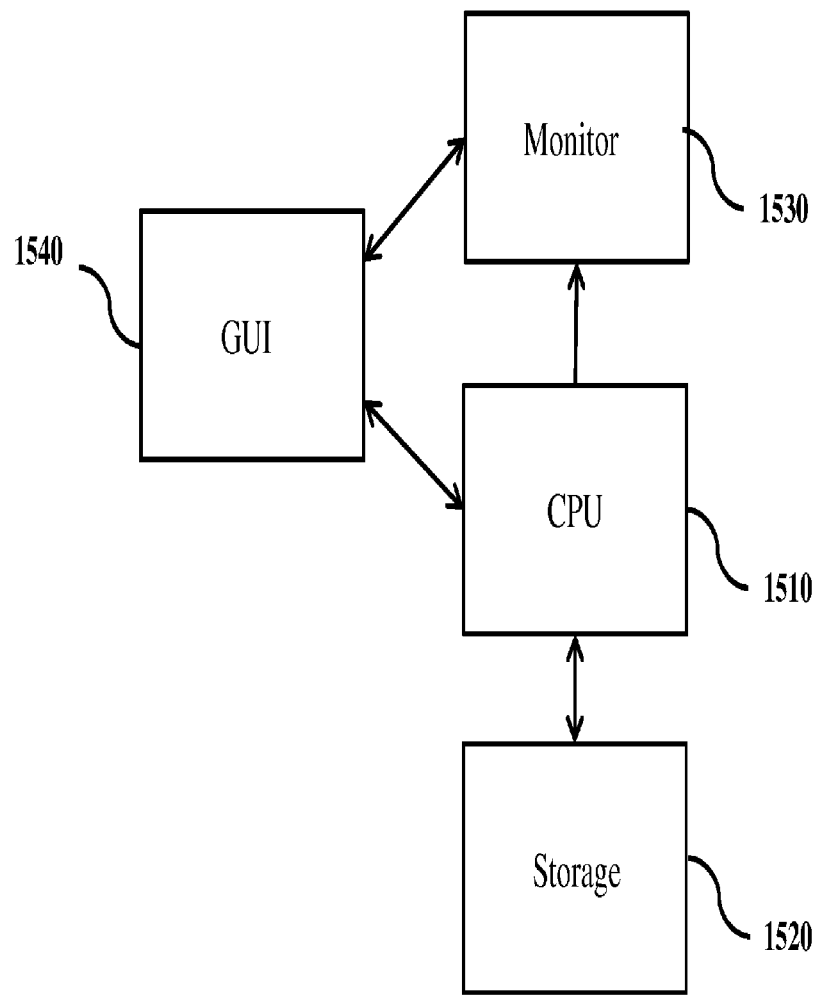
FIG. 15 is a block diagram for a system for indicating parameters in an imaging data set.

In order to construct the images, the collected reflectivity measurements are processed with various computer or processor-based systems which compile data from measurements into a pictorial format. For example, the system described in FIG. 14 may be used to construct intraluminal images from OCT probe measurements, and optionally display the images to a user of the OCT system. In some embodiments, a user interacts with a visual interface to view images from the imaging system. Input from a user (e.g., parameters or a selection) are received by a processor in an electronic device. The selection can be rendered into a visible display. An exemplary system including an electronic device is illustrated in FIG. 14. As shown in FIG. 14, imaging engine 859 communicates with host workstation 2433 as well as optionally server 2413 over network 2409.

In some embodiments, an operator uses computer 2449 or terminal 2467 to control system 2400 or to receive images. An image may be displayed using an I/O 2454, 2437, or 2471, which may include a monitor. An I/O may include a keyboard, mouse or touchscreen to communicate with any of processor 2421, 2459, 2441, or 2475, for example, to cause data to be stored in any tangible, nontransitory memory 2463, 2445, 2479, or 2429. Server 2413 generally includes an interface module 2425 to effectuate communication over network 2409 or write data to data file 2417.

System 2400 may be used to execute instructions to display images in an interactive format, e.g., with indicators, as described above. Alternatively, an imaging data set may be assessed, analyzed, and transformed with a system comprising CPU 1510, storage 1520, and monitor 1530. Storage 1520 may contain instructions for carrying out methods of the invention, e.g., to configure CPU 1510 to analyze the imaging data set for a parameter, assign an indicator to the medical device based on the presence of the parameter, and display the indicator on monitor 1530. For example CPU 1510 may direct monitor 1530 to display a longitudinal image of a lumen with a color-coded stent. In some embodiments, a system of the invention will additionally comprise graphical user interface (GUI) 1540, which allows a user to interact with the images. In some embodiments, CPU 1510, storage 1520, and monitor 1530 may be encompassed within system 2400.

The systems and methods of use described herein can be performed using any type of computing device, such as a computer, that includes a processor or any combination of computing devices where each device performs at least part of the process or method. In some embodiments, systems and methods described herein may be performed with a handheld device, e.g., a smart tablet, or a smart phone, or a specialty device produced for the system.

In some embodiments, a device of the invention includes an OCT imaging system and obtains a three-dimensional data set through the operation of OCT imaging hardware. In some embodiments, a device of the invention is a computer device such as a laptop, desktop, or tablet computer, and obtains a three-dimensional data set by retrieving it from a tangible storage medium, such as a disk drive on a server using a network or as an email attachment.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer program include, by way of example, both general and special purpose microprocessors, and any one or more processor of any kind of digital computer. Generally, a processor will receive instructions and data from a read-only memory or a random access memory or both. The essential elements of computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through network by any form or medium of digital data communication, e.g., a communication network. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

Exemplary step-by-step methods are described schematically in FIGS. 16A-D. It will be understood that each block of FIGS. 16A-D, as well as any portion of the systems and methods disclosed herein, can be implemented by computer program instructions. These program instructions may be provided to a processor to produce a machine, such that the instructions, which execute on the processor, create means for implementing the actions specified in the FIGS. 16A-D or described for the systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes or even in a different sequence than illustrated without departing from the scope or spirit of the invention.

Figures 16A, 16B:
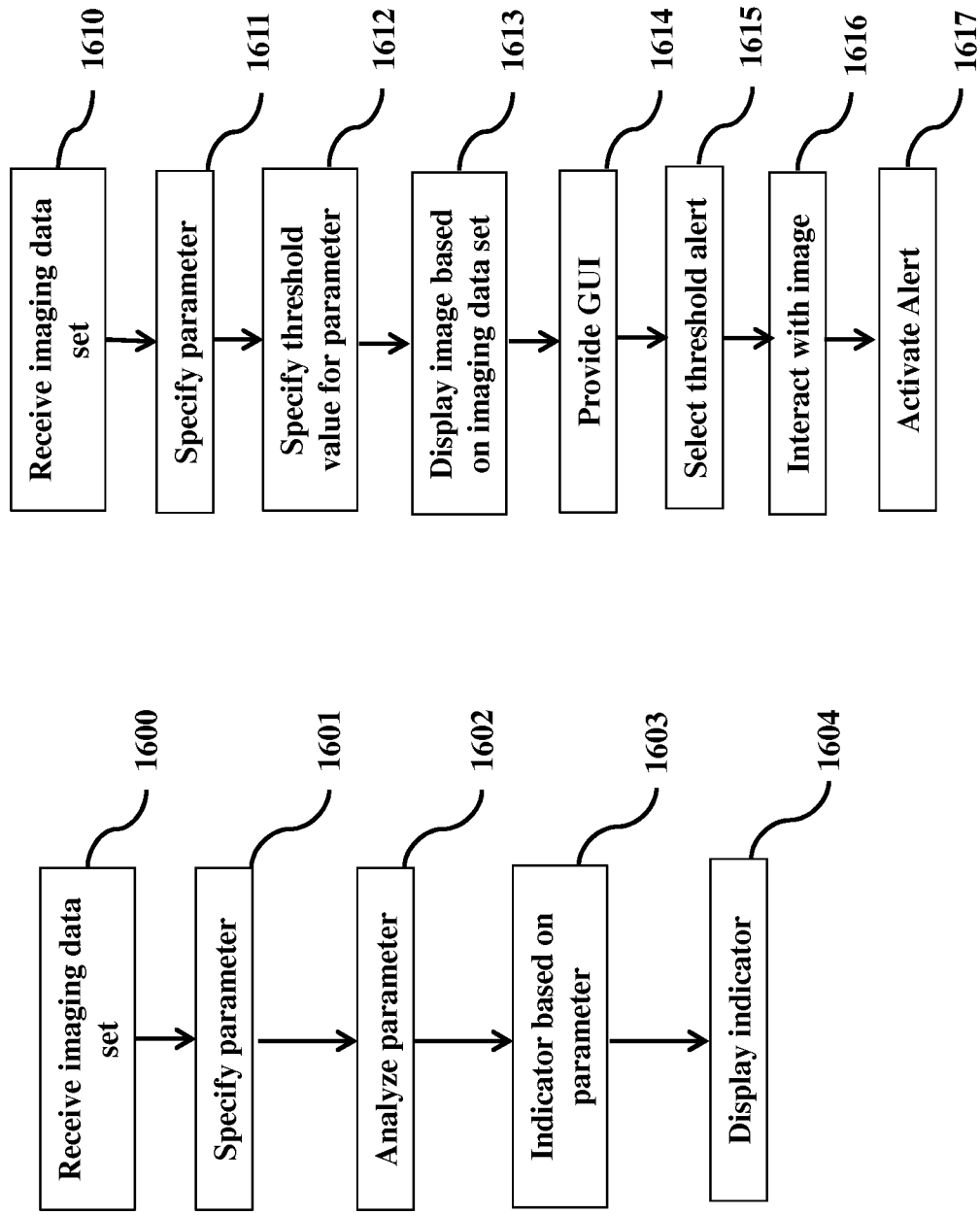
FIG. 16A shows block diagrams for the procedural steps in color coding a medical device in a medical image.
FIG. 16B shows block diagrams for assigning a user alert to an image property.
Figures 16C, 16D:
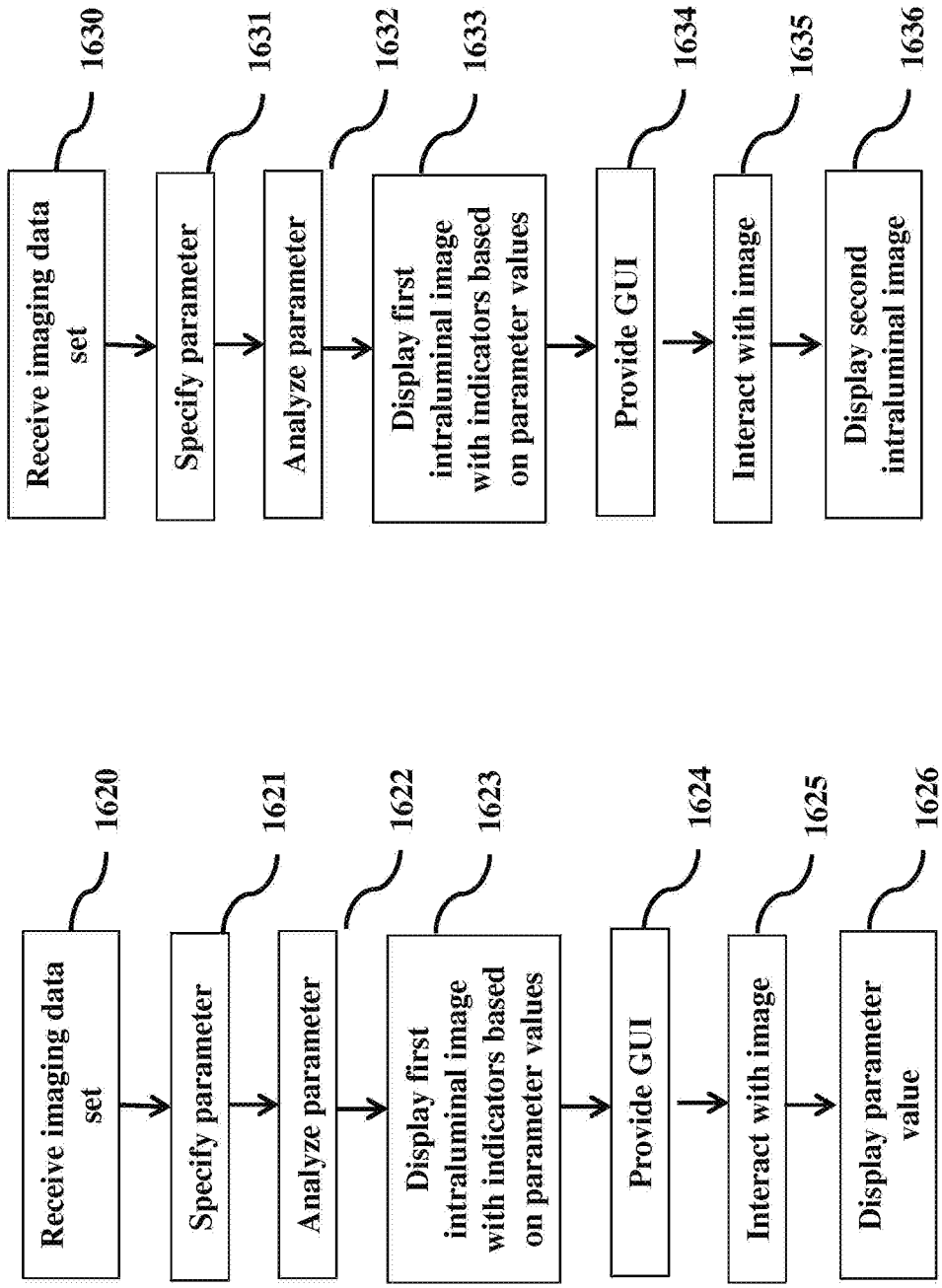
FIG. 16C shows block diagrams for interacting with an image to display a parameter value.
FIG. 16D shows block diagrams for interacting with an image to display a secondary image.

A basic function of a system of the invention is described in FIG. 16A in which an image data set is received, one or more parameters is specified and analyzed, an indicator is selected, and the indicator is displayed. In some instances, e.g., as shown in FIG. 16B a threshold value of the parameter will be defined by the user, however in other instances this is not necessary. Additionally, as shown in FIG. 16B the user may be provided with a GUI to set a threshold alert and interact with the images, thereby triggering an alert when the threshold value is exceeded. In alternative embodiments, e.g., as shown in FIGS. 16C and 16D, a user may also cause parameter values to be displayed or cause additional images to be displayed by interacting with the GUI.

Threshold analysis can be completed using algorithms known in the field of image analysis. For example, a value input by a user may be converted into a threshold level which will be applied to one or more pixels of a B-scan image (e.g., FIG. 12). When the level of the measured pixels is greater than the threshold value, the corresponding pixels in the scan converted image (e.g., FIG. 13) will be displayed in green. When the level of the pixels is less than the threshold value, the corresponding pixels in the scan converted image (e.g., FIG. 13) will be displayed in red. The method can be extended to produce multicolored displays by using threshold ranges, i.e., multiband thresholding. In some instances, the threshold levels maybe preset, or the user may select from a list or preset levels, for example, by selecting levels from a pull-down menu in the GUI.

In other instances, automatic thresholding may be used, wherein an image data set is analyzed to determine a distribution of levels of pixels for a location in the images (e.g., the OCT B-scans), the median of the distribution is set as the threshold, and then pixels of images which fall above and below the threshold may be colored appropriately. In some embodiments, only the pixels that fall outside of a statistical range will be color coded.

It is also intended that a user could define a threshold which will correspond to an aspect of a scan converted image (e.g., FIG. 13) or a longitudinal or 3D view of a lumen. For example, a user could define a threshold for a minimum lumen area. The system would automatically determine a lumen area for each segment of the lumen based upon an analysis of the B-Scan or the scan converted image, and then compare the threshold for a minimum lumen area to the determined lumen area for each segment. Segments having a lumen area less than the minimum lumen area could be color-coded red, for example.

Figure 17:
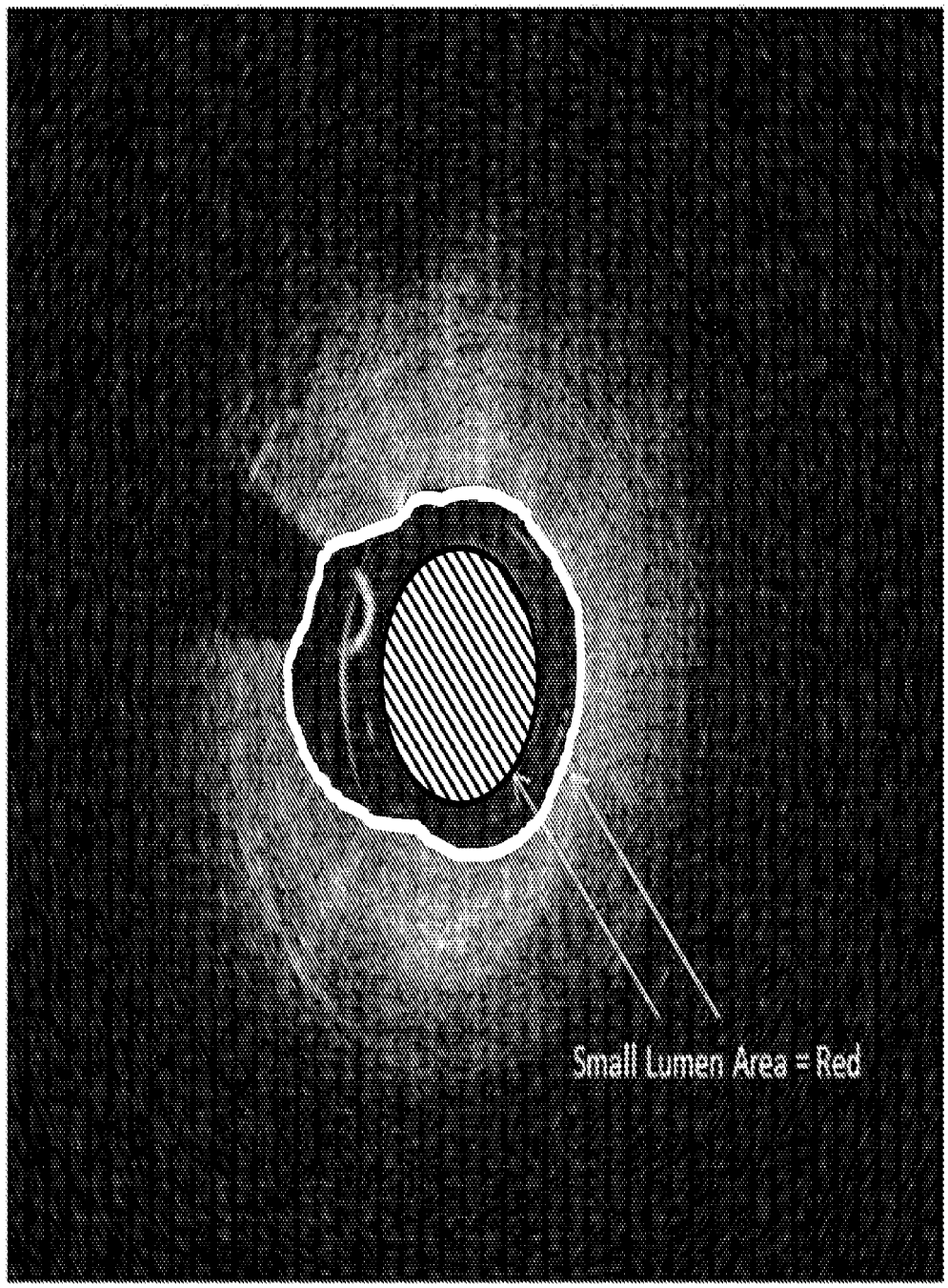
FIG. 17 illustrates a color-coded lumen indicating that the cross sectional area of a vessel lumen is smaller than a predetermined threshold value.
Figure 18:
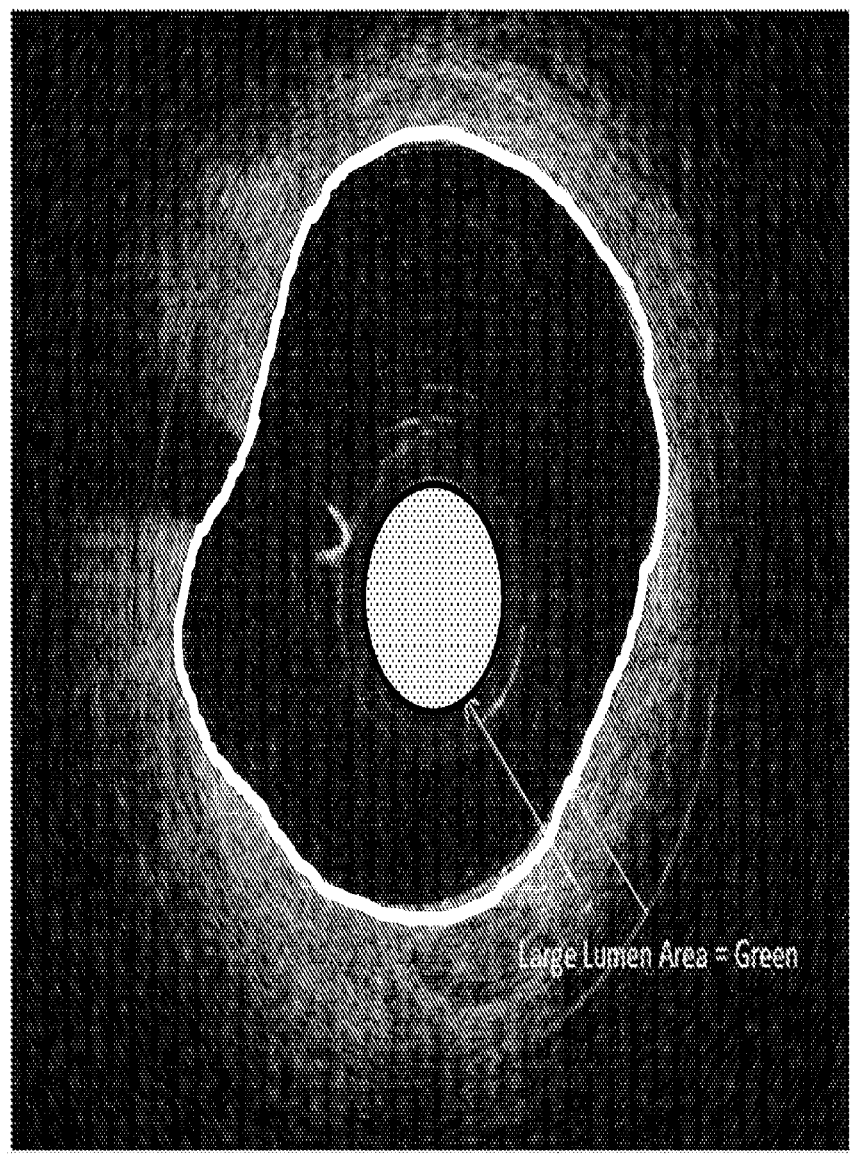
FIG. 18 illustrates a color-coded lumen indicating that the cross sectional area of a vessel lumen is larger than a predetermined threshold value.
Figure 19:
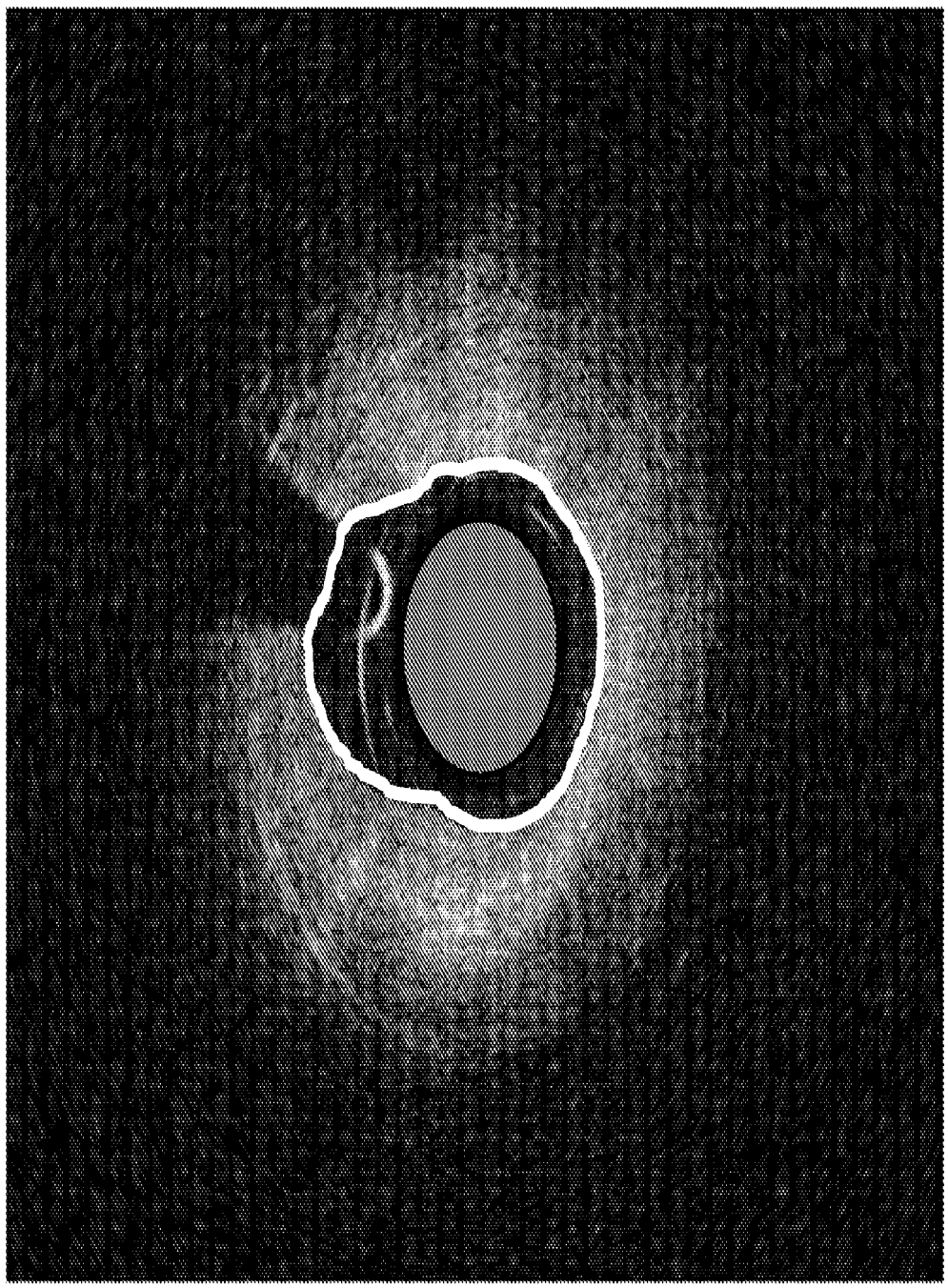
FIG. 19 illustrates a color-coded lumen as in FIG. 17, with the color coding of the lumen showing transparency.
Figure 20:
FIG. 20 illustrates a color-coded lumen as in FIG. 18, with the color coding of the lumen showing transparency.
Figure 21A:
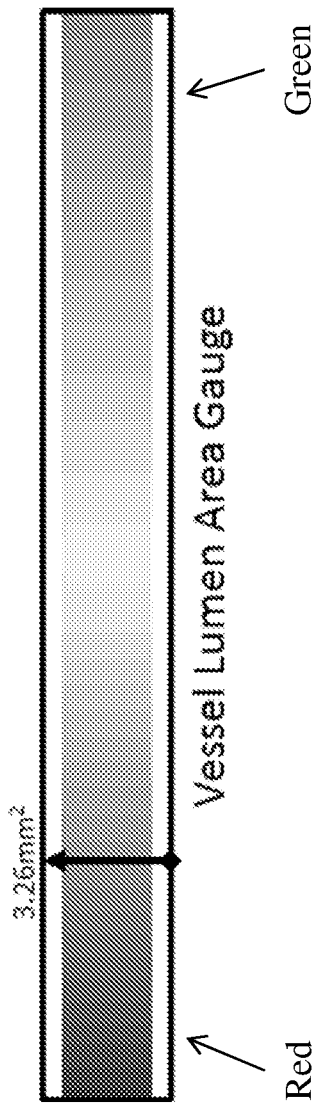
FIG. 21A shows exemplary indicators that may be used to indicate values of parameters.

Systems and methods of the invention provide images of lumen where parameters are displayed as indicators to assist a user in identifying key features which may be indicative of a disease or disorder. For example, a user may set a threshold value for a diameter of a lumen to be imaged with OCT. When the user views the images of a lumen, an indicator, e.g., a color code, is also displayed atop the image as shown in FIGS. 17 and 18. In the instance of a lumen having a lumen area smaller than the threshold (FIG. 17), the perimeter of the lumen may be colored red or a red dot may be displayed in the center of the image. In the instance of a lumen having a lumen area greater than the threshold (FIG. 18), the perimeter of the lumen may be colored green or a green dot may be displayed in the center of the image. Various other indicators could be used in the image, for example a prominent "X" for the lumen having a lumen area less than the threshold, and a prominent check mark for the lumen having a lumen area greater than the threshold. Combinations of colors and marks would also be suitable. To the extent that the displayed indicators obstructed the view of key image features, the indicators can be made partially transparent, e.g., as shown in FIGS. 19 and 20, where the images of FIGS. 17 and 18 (respectively) are marked with semi-transparent indicators. In other embodiments, the user may be able to toggle the indicators on or off, for example by "right-clicking" on the image and selecting to turn off the indicators. While not shown in the FIGS., it is envisioned that, in some embodiments, a user can call up specific values of a parameter, e.g., a diameter of a lumen, by interacting with the image. Alternatively, interacting with the image may trigger a visual, audio, or haptic alert. In some embodiments, interacting with the image may prompt display of values of a parameter in another visual format, for example as a gauge, such as the gauge displayed in FIG. 21A. Combinations of the above listed indicators and alerts are also possible.

In other embodiments, it will be advantageous to display measurements of a lumen in a longitudinal format, e.g., as shown in FIG. 22. As shown in FIG. 22, a number of B-scans are laid end-to-end, and a cut away is produced as if looking down into the lumen. Like the cross-sectional views of FIGS. 17-20, the perimeter of the longitudinal image can be color coded to indicate values of a parameter, e.g., with respect to a threshold value or with respect to each other. In some embodiments, the volume of the cut away can be filled with color or other symbols to indicate areas of concern.

As shown in FIG. 22, sections of the lumen in which the diameter is smaller than a threshold can be shaded with one color, e.g., red, and sections of the lumen in which the diameter is larger than a threshold can be shaded with another color e.g., green. Alternatively, the diameters can be indicated with shaded regions. In FIG. 22, a constricted region is indicated with a darker box while an unconstricted region is indicated with a lighter box. In other embodiments (not shown) a longitudinal view of the lumen may be displayed and a user can call up specific values of a parameter, e.g., a diameter of a lumen, by interacting with the image. Alternatively, interacting with the image may trigger a visual, audio, or haptic alert. For example, the user could drag a mouse pointer along the length of the longitudinal image and receive a haptic alert when the pointer is in a region of occlusion.

Figure 24:
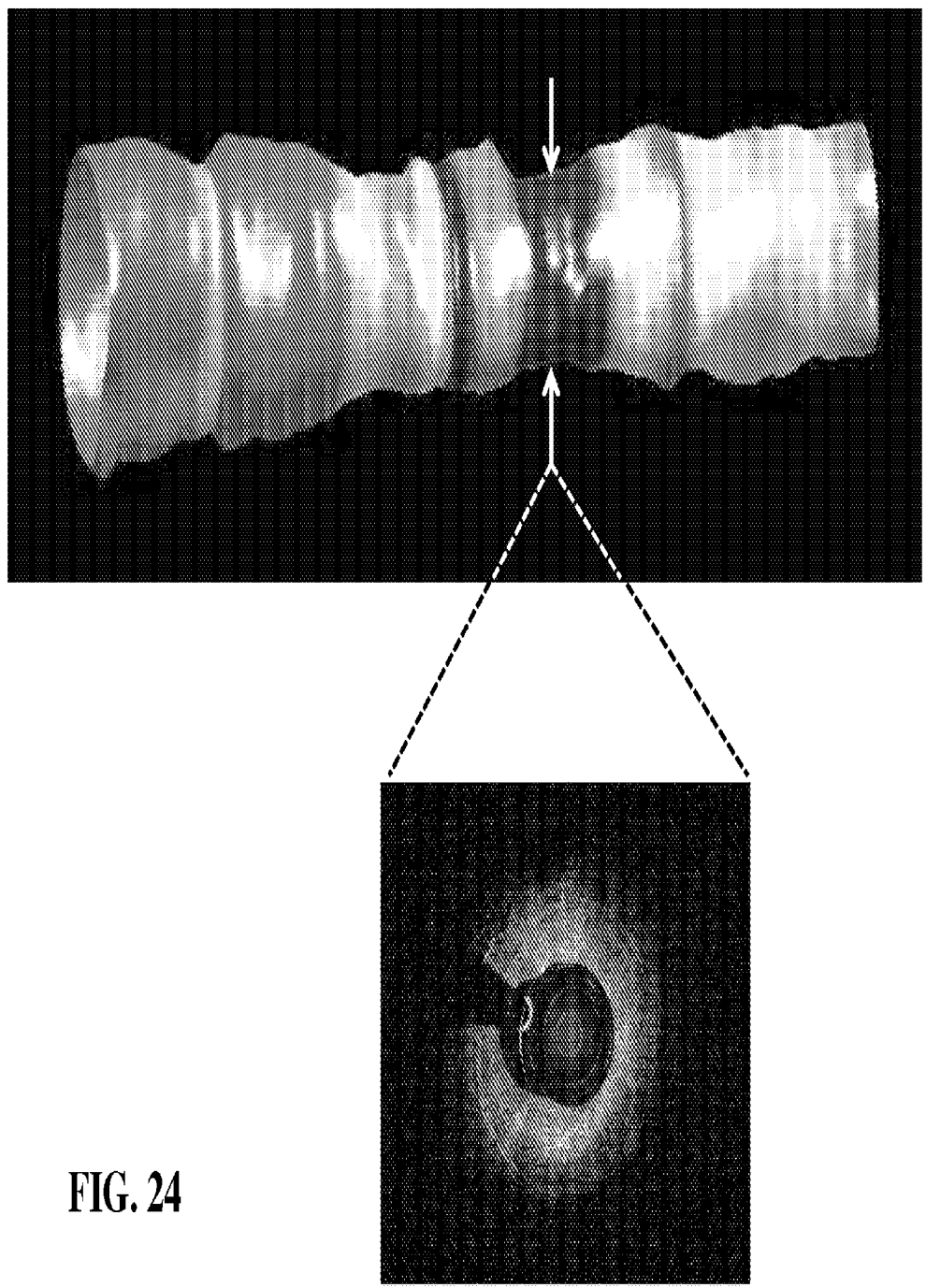
FIG. 24 illustrates the use of a graphical user interface to interact with an image and to prompt display of a second related image.

In other embodiments, it will be advantageous to display measurements of a lumen in a three-dimensional format, e.g., as shown in FIG. 23. As shown in FIG. 23, a number of B-scans are laid end-to-end, and a three-dimensional view of the lumen is produced. The three-dimensional view may be color-coded to indicate values of a parameter, e.g., with respect to a threshold value or with respect to each other. As shown in FIG. 23, sections of the lumen in which the diameter is smaller than a threshold can be shaded with one color, e.g., red, and sections of the lumen in which the diameter is larger than a threshold can be shaded with another color, e.g., green. Intermediate regions may be shaded with a third color, e.g., yellow. The image may be scaled with hundreds of colors spanning from red to green. In other embodiments (not shown) a three-dimensional view of the lumen may be displayed and a user can call up specific values of a parameter, e.g., a diameter of a lumen, by interacting with the image. Alternatively, interacting with the image may trigger a visual, audio, or haptic alert. For example the user could drag a mouse pointer along the length of the three-dimensional image and receive a haptic alert when the pointer is in a region of occlusion. In other embodiments, a user can click on a region of interest and bring up an alternative image, e.g., a cross sectional image, as shown in FIG. 24.

In certain embodiments a user can employ an indicator such as navigation line, a cursor, a callout marker or the like to identify an image plane in an image being viewed. For example, a three-dimensional image of a vessel can be constructed from a set of two-dimensional image frames. A user can scroll over the three-dimensional image with an indicator to identify a particular image frame corresponding to the location of the indicator on the image, as shown in FIG. 24. The particular image frame can be selected and displayed in a two-dimensional format. In certain embodiments, as a user scrolls an indicator over or through a three-dimensional image with one or more image frame having a diagnostic property at a predefined threshold, the user will be alerted by the computer as described herein.

Figure 21B:
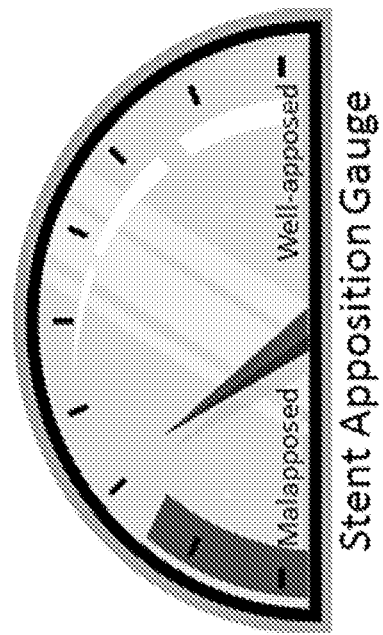
FIG. 21B shows exemplary indicators that may be used to indicate values of parameters.
Figure 25:
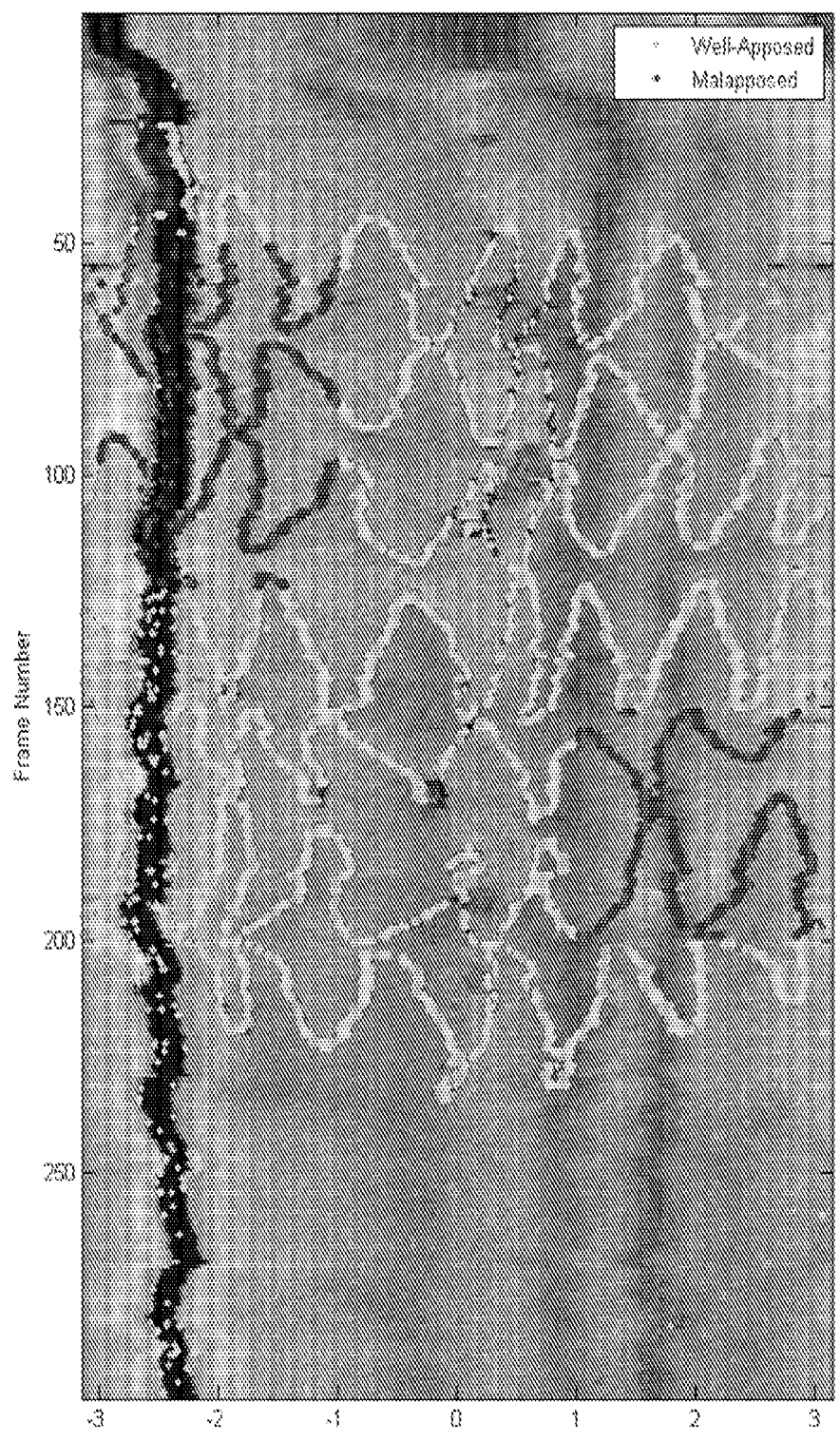
FIG. 25 illustrates a splayed view of a stent placed within a lumen wherein the stent is color-coded to indicate apposition.

Using the systems and methods of the invention it is also possible to analyze and display images of medical devices with indicators relating to a parameter. As shown in FIG. 25, a splayed B-scan of a stent within a lumen can be displayed with values of apposition indicated with various colors. (In a splayed B-scan the luminal walls of a three-dimensional construct, i.e., FIG. 23, are unrolled into a two dimensional sheet.) In FIG. 25, the stent is visible as zigzag pattern across the image. Portions of the stent that display incomplete apposition ("malapposed") are shown in a dark color, while portions of the stent that are properly apposed are shown in a lighter color. In alternative embodiments, a user could interact with the image of the stent and trigger an alert, for example, when a portion of the stent displayed incomplete apposition. In other embodiments, a user could call up specific values of a parameter, e.g., apposition of the stent, by interacting with the image. In another embodiment, a user may cause a stent apposition gauge to be displayed, such as shown in FIG. 21B.

While other methods are known, systems of the invention may use edge detection algorithms to determine the boundaries of the stent and the corresponding overlap (or lack thereof) with the lumen wall. Edges of the stent may be detectable in the A-scans as pronounced changes in reflectivity, i.e., a reflectivity change of more than 10%, more than 30%, more than 50%, or more than 100%, within less than 5 mm, less than 3 mm, less than 2 mm, or less than 1 mm radial distance. A front and back radial edge of the stent can be found by determining the location of two edges in the A-scan. Alternatively, stents may be located in B-scans by determining regions of pronounced change in pixel levels, corresponding to the change in reflectivity of the A-scan discussed above.

A value for the apposition of a stent may be determined by combining stent edge detection with methods for identifying lumen borders, i.e., lumen walls. The lumen border can be automatically or semi-automatically detected in an image using any method known in the art, such as the techniques disclosed in U.S. Pat. No. 7,978,916, S. Tanimoto, G. Rodriguez-Granillo, P. Barlis, S. deWinter, N. Bruining, R. Hamers, M. Knappen, S. Verheye, P. W. Serruys, and E. Regar, "A novel approach for quantitative analysis of intracoronary optical coherencetomography: High inter-observer agreement with computer-assisted contour detection," *Cathet. Cardiovasc. Intervent.* 72, 228-235 (2008); K. Sihan, C. Botka, F. Post, S. deWinter, E. Regar, R. Hamers, and N. Bruining, "A novel approach to quantitative analysis of intraluminal optical coherence tomography imaging," *Comput. Cardiol.* 1089-1092 (2008); J. Canny, "A computational approach to edge detection," *IEEE Trans. Pattern Anal. Mach. Intell.* 8, 679-698 (1986), all incorporated herein by reference in their entireties.

In one embodiment, a value for the apposition can be determined by subtracting the radial distance of the front radial edge of the lumen border from the back radial edge of the stent. A positive value indicates a gap or a malapposed stent. A zero value or negative value would indicate that there was no gap, or that tissue had partially covered the stent. In some embodiments, the stent would be color coded to indicate that a portion of the stent was not in contact with the lumen border. In some embodiments, a scan converted image corresponding to a segment of the lumen with a malapposed stent will be color coded, or will be identified with an alert to facilitate identification by a user.

Figure 26:
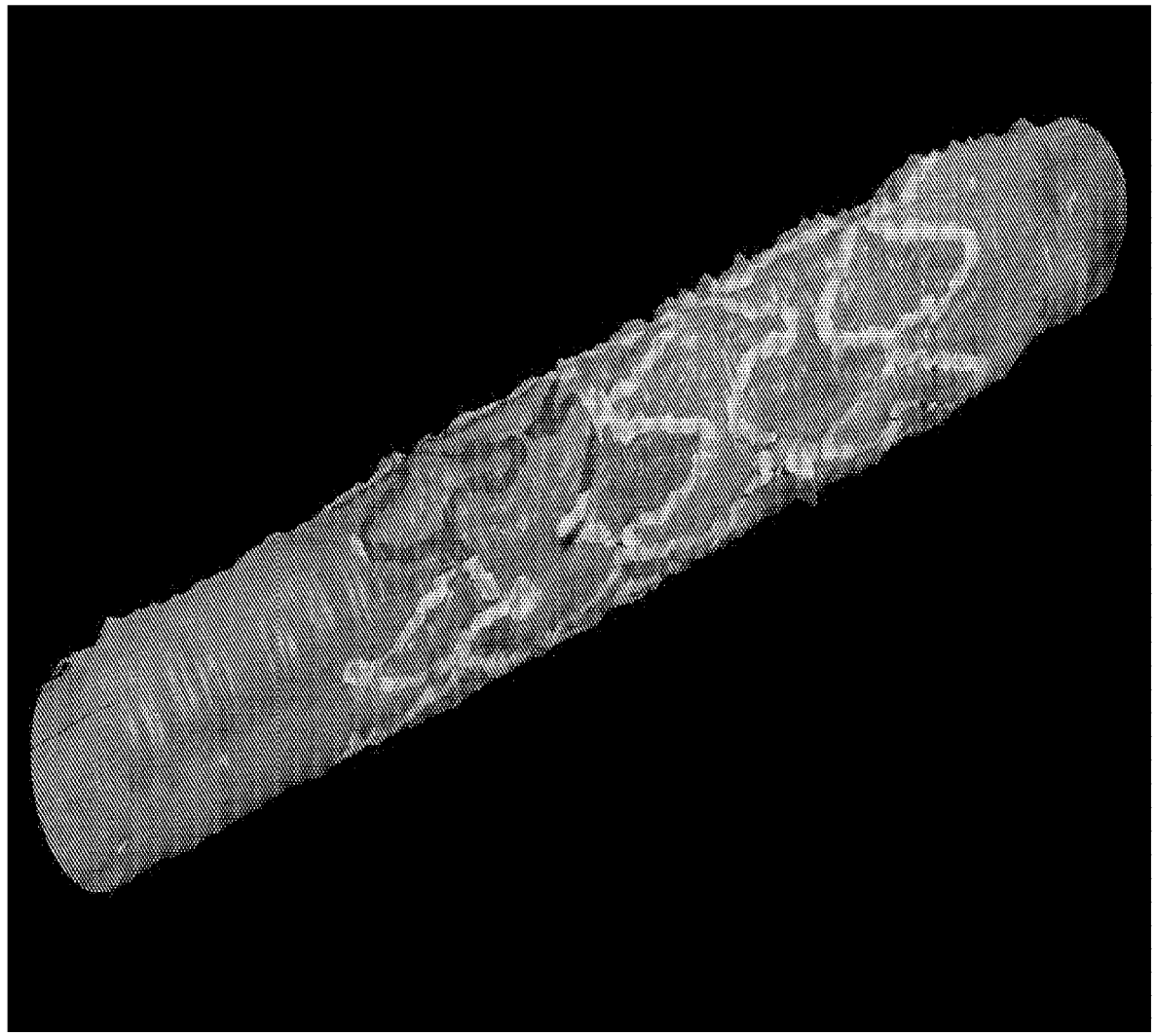
FIG. 26 illustrates a three-dimensional view of a stent placed within a lumen wherein the stent is color-coded to indicate apposition.

In an alternative embodiment, as shown in FIG. 26, the stent and the lumen can be shown simultaneously in a three-dimensional view. Portions of the stent that display incomplete apposition are shown in a dark color and portions of the stent that are properly apposed are shown in a lighter color.

Figure 27:
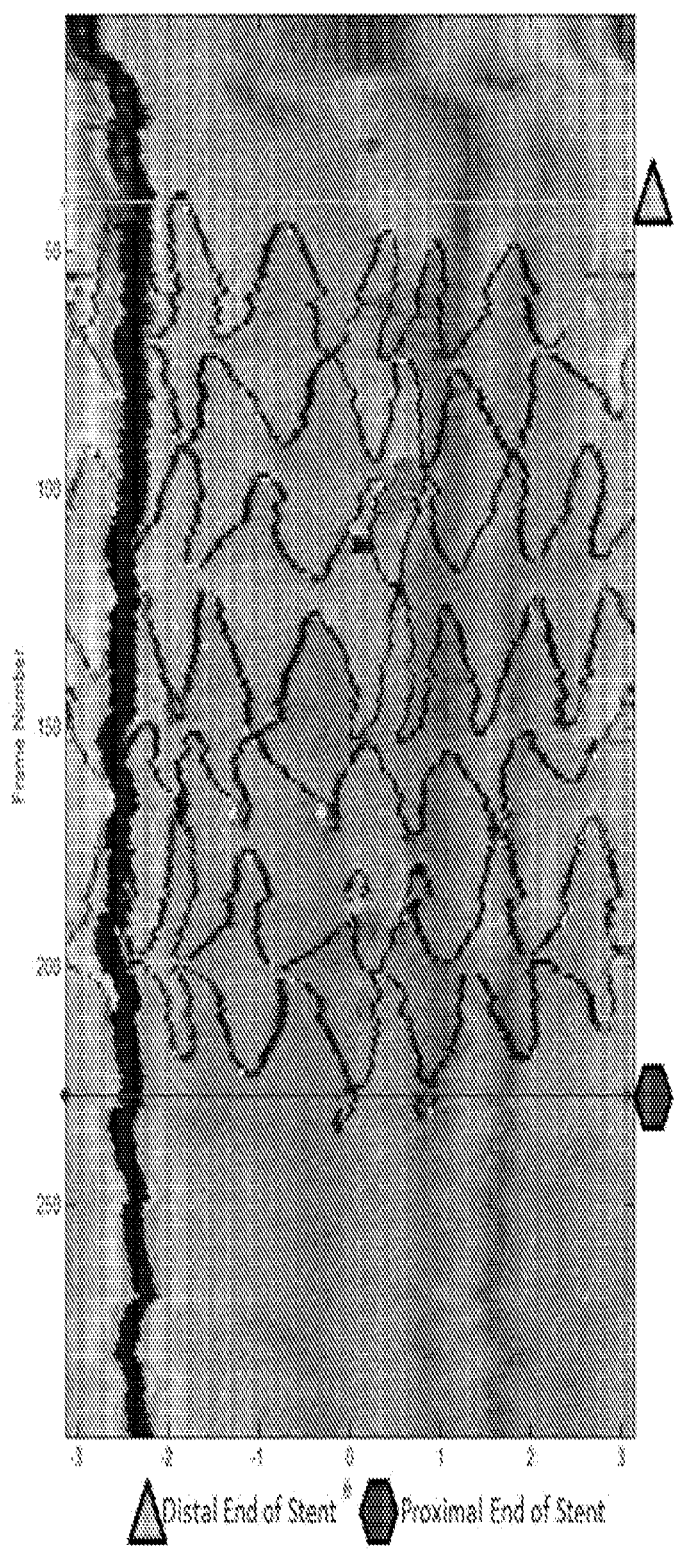
FIG. 27 illustrates a splayed view of a stent placed within a lumen wherein markers are used to set boundaries for an analysis of the image.

In other embodiments, the user may interact with a portion of an image to set a range for identification of a parameter. For example, as shown in FIG. 27, a user may set the limits of a luminal image to be processed for a parameter, e.g., stent apposition, and the system of the invention will overlay indicators based on the parameter only in the region of interest.

Systems and methods of the invention include image-processing techniques that provide automatic detection of objects, such as stents, within intraluminal images. Typically, the OCT intraluminal image is an intravascular image taken within a lumen of a blood vessel, but the detection methods described herein can be used to detect objects within other biological lumens, such as the intestine. Although the following description is directed towards detecting objects in OCT images, one skilled in the art would readily recognize that methods and systems of intention can be utilized to detect objects in any intraluminal images obtained from any other imaging technique, such as intravascular ultrasound imaging (IVUS) and combined OCT-IVUS.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. An intravascular imaging system, comprising:
    an intravascular imaging catheter configured to be positioned within a lumen of a blood vessel and obtain imaging data of a wall of the blood vessel and a stent surrounding the lumen; and
    a processor configured to:
        receive the imaging data obtained by the intravascular imaging catheter;
        identify a first portion of the imaging data representative of the wall of the blood vessel;
        identify a second portion of the imaging data representative of the stent;
        determine, based on the first and second portions of the imaging data, an apposition value of the stent relative to the wall of the blood vessel for each of a plurality of locations of the stent; and
        output, to a display in communication with the processor, a graphical representation indicating the apposition value for each of the plurality of locations of the stent;
    wherein the processor is further configured to determine the apposition value for each of the plurality of locations of the stent by:
        determining a positive apposition value if there is a gap between the position of the stent and the position of the wall of the blood vessel;
        determining a negative apposition value if there is tissue overlapping the stent; and
        determining an apposition value of zero if there is no gap and tissue does not overlap the stent.

2. The system of claim 1, wherein the processor is configured to:
    receive a user input identifying a region of the stent, wherein the user input includes identifying a location on the graphical representation; and
    output, to the display in communication with the processor, a graphical element proximate to the location on the graphical representation, wherein the graphical element includes the apposition value associated with the region of the stent identified by the user input.

3. The system of claim 1, wherein the user input indicates a proximal boundary and a distal boundary of the area of the image to be processed.

4. The system of claim 3, wherein the processor is further configured to output, to the display based on the input, a visual representation of the proximal boundary and the distal boundary.

5. The system of claim 1, wherein the intravascular imaging catheter comprises an IVUS imaging catheter.

6. The system of claim 1, wherein the processor is configured to:
    determine, based on the first portion of the imaging data, a first radial distance of the wall of the lumen;
    determine, based on the second portion of the imaging data, a second radial distance of a back edge of the stent; and
    determine the apposition value based on a subtraction of the first radial distance from the second radial distance.

7. The system of claim 1, wherein the graphical representation comprises at least one of a callout marker, a gauge, or a numerical indicator.

8. The system of claim 1, wherein the graphical representation includes an image of the stent.

9. The system of claim 8, wherein the image of the stent is a two-dimensional image.

10. The system of claim 8, wherein the image of the stent is a three-dimensional image.

11. The system of claim 8, wherein the image of the stent is representative of the wall of the lumen and the stent positioned on the wall of the lumen.

12. The system of claim 11, wherein different portions of the stent are given different visual characteristics in the image based on a corresponding apposition value for each of the different portions.

13. The system of claim 12, wherein the different visual characteristics comprise different colors.

14. The system of claim 1, wherein the graphical representation includes an indicator of the area on the image.

15. The system of claim 1, wherein the processor is further configured to generate an alert when a portion of the stent is malapposed.

16. The system of claim 15, wherein the alert comprises a visual alert.

17. The system of claim 15, wherein the alert comprises an audio alert.

18. The system of claim 15, wherein the alert comprises a haptic alert.

19. The system of claim 1, wherein the graphical representation is a three-dimensional graphical representation comprising:
- a three-dimensional graphical representation of the wall of the blood vessel; and
- a three-dimensional graphical representation of the stent, wherein each of the plurality of locations of the stent are displayed according to the apposition value for each of the plurality of locations of the stent.

* * * * *